United States Patent
Lee et al.

(10) Patent No.: US 6,514,935 B1
(45) Date of Patent: Feb. 4, 2003

(54) METHODS OF TREATING HYPERTENSION

(75) Inventors: Mu-En Lee, Newton, MA (US); Shaw-Fang Yet, Andover, MA (US)

(73) Assignee: President and Fellows of Harvard, Cambridge, MA (US)

( * ) Notice: Subject to any disclaimer, the term of this patent is extended or adjusted under 35 U.S.C. 154(b) by 0 days.

(21) Appl. No.: 09/305,839

(22) Filed: May 5, 1999

Related U.S. Application Data

(63) Continuation-in-part of application No. 08/818,655, filed on Mar. 14, 1997, now Pat. No. 6,258,557.

(51) Int. Cl.$^7$ ............................................. A61K 38/00

(52) U.S. Cl. .......................................................... 514/2

(58) Field of Search ............................................. 514/2

(56) References Cited

U.S. PATENT DOCUMENTS

| | | |
|---|---|---|
| 5,585,479 A | 12/1996 | Hoke et al. |
| 5,767,262 A | * 6/1998 | Lee et al. |
| 5,990,092 A | * 11/1999 | Walsh et al. |
| 6,136,953 A | * 10/2000 | Lee et al. |

FOREIGN PATENT DOCUMENTS

| | | | |
|---|---|---|---|
| WO | WO 97/33901 | 3/1996 | ........... C07H/21/00 |
| WO | WO 97/33901 | 9/1997 | |
| WO | WO 98/18822 | 5/1998 | |

OTHER PUBLICATIONS

Attwood The Babel of Bioinformatics Science vol. 290 Oct. 20, 2000.*

Jain et al., Molecular cloning and characterization of SmLIM, a developmentally regulated LIM protein preferentially expressed in aortic smooth muscle cells, 1996, The Journal Of Biological Chemistry, vol. 271, pp. 10194–10199.*

Arber et al., "Muscle LIM Protein, a Novel Essential Regulator of Myogenesis, Promotes Myogenic Different–iation", Cell, 79:221–31 (1994).

Bredt et al., "Localization of nitric oxide synthase indicating a neural role for nitric oxide," Nature, 347:768–70 (1990).

Crawford et al., "Biochemical and Molecular Characterization of the Chicken Cysteine–rich Protein, a Developmentally Regulated LIM–Domain Protein That Is Associated with the Actin Cytoskeleton", J. Cell Biol. 124:117–27 (1994).

Doetschman et al., "The in virto development of blastocyst–derived embryonic stem cell lines: formation of visceral yolk sac. blood islands and myocardium," J. Embroyol. Exp. Morph., 87:27–45 (1985).

Lee et al., "The Type I Iodothyronine 5'–Deiodinase Messenger Ribonucleic Acid Is Localized to the S3 Segment of the Rat Kidney Proximal Tubule," Endocrinology, 132:2136–40 (1993).

Libby et al., "Biology of Disease: Involvement of the Immune System in Human Atherogenesis: Current Knowledge and Unanswered Questions", Lab Investig., 64:5–15 (1991).

Liebhaber et al., "Charcterization of a Human cDNA Encloding a Widley Expressed and Highly Conserved Cysteine–rich Protein with an Unusual Zinc–finger Motif", Nucleic Acids Research, 18:3871–79 (1990).

Melani et al., "Charcterization of a human cDNA encoding a widely expressed and highly conserved cysteine–rich protein with an unusual zinc–finger motif", Cancer Res., 51:2879–901 (1991).

Munro et al., "Biology of Diseases: The Pathogenesis of Atherosclerosis: Atherogenesis and Inflammation", Lab. Invest., 58:249–61 (1988).

Pennica et al., Cloning and expression of human tissue–type plasminogen activator cDNA in *E. coli*, Nature 301:214 (1982).

Ross, The Pathogenesis of Atheroscierosis: a Perspective for the 1990's, Nature, 362:801–809 (1993).

Sadler et al., "Zyxin and CCRP: Two Interactive LIM Doamin Proteins Associated with the Cytoskeleton", J. Cell Biol., 119:1573–87 (1992).

Tsai et al., "Promotion of Vascular Smooth Muscle Cell Growth by Homocysteine: A Link to Atheroscierosis", PNAS USA, 91:6369–73 (1994).

Wang et al., "Analysis of the Human Cystene–Rich Protein Gene (CSRP) Assignment to Chromosome 1q24–1q32, and Identification of an Associated Mspl. Polymorphism", Genomics 14:391–97 (1992).

Wang et al., "Human Cysteine–rich Protein: A Member of the Lim/Double–Finger Family Displaying Coordinate Serum Induction with c–myc", J. Biol. Chem., 267:9176–84 (1992).

Warren et al., "The Oncogenic Cysteine–Rich LIM Domain Protein Rbtn2 is Essential for Erythoid Development" Cell, 78:45–57 (1994).

Weiskirchen et al., "The Cysteine–rich Protein Family of Highly Related LIM Domain Proteins", J. Biol. Chem. 270:28946–54 (1995).

Weiskirchen et al., "Suppression in Transformed Avian Fibroblasts of a Gene (crp) Encoding a Cysteine–rich Protein Containing LIM Domains", Oncogene 8:2317–24 (1993).

Williams et al., "Introduction of foreign genes into tissues of living mice by DNA–coated microprojectiles," PNAS USA, 88:2726–29 (1991).

(List continued on next page.)

*Primary Examiner*—Remy Yucel
*Assistant Examiner*—Konstantina Katcheves
(74) *Attorney, Agent, or Firm*—Ingrid A. Beattie; Mintz Levin Cohn Ferris Glovsky & Popeo

(57) ABSTRACT

The invention features a method of inhibiting hypertension in a mammal by administering to the mammal a compound that reduces expression or activity of SmLIM.

3 Claims, 11 Drawing Sheets

OTHER PUBLICATIONS

Tsai et al., "Induction of Cyclin A Gene Expression by Homocysteine in Vascular Smooth Muscle Cells", The Journal of Clinical Investigation, vol. 97, No. 1, 1996, p. 146–153.

Hiller et al., GenBank Accession #N39473, Jan. 19, 1996.

Arber S., et al., Muscle LIM Protein, a Novel Essential Regulator of Myogenesis, Promotes Myogenic Differentiation, Cell 79: 221–231, Oct. 21, 1994.

Bredt, D. S., et al., Localization of Nitric Oxide Synthase Indicating a Neural Role for Nitric Oxide. Nature 347: 768–770, Oct. 25, 1990.

Crawford, A. W., et al., Biochemical and Molecular Characterization of the Chicken Cysteine–rich Protein, a Developmentally Regulated LIM–Domain Protein that is Associated with the Actin Cytoskeleton. JCB 124(1&2): 117–127, Jan. 1994.

Doetschman, T. C., et al., The In Vitro Development of Blastocyst–derived Embryonic Stem Cell Lines: Formation of Visceral Yolk Sac, Blood Islands and Myocardium. J. Embryol. exp. Morph. 87: 27–45 (1985).

El–Deiry, W.S., et al., WAF1, a Potential Mediator of p53 Tumor Suppression. Cell 75: 817–825, (Nov. 19, 1993).

Hillier, L., et al., GenBank Accession #: N39473, (Jan. 19, 1996).

Jain, M.K., et al., Molecular Cloning and Characterization of SmLIM, a Developmentally Regulated LIM Protein Preferentially Expressed in Aortic Smooth Muscle Cells. JBC 271(17): 10194–10199, (Apr. 26, 1996).

Lee, W–S., et al., The Type I Iodothyronine 5'—Deiodinase Messenger Ribonucleic Acid Is Localized to the S3 Segment of the Rat KidneyProximal Tubule. Endocrinology 132(5): 2136–2140, (1993).

Libby, P., and Hansson, G.K. Involvement of the Immune System in Human Artherogenesis: Current Knowledge and Unanswered Questions. Laboratory Investigation 64(1): 5–15, (1991).

Liebhaber, S. A., et al, Characterization of a Human cDNA Encoding a Widely Expressed and Highly Conserved Cysteine–rich Protein with an Unusual Zinc–finger Motif. Nucleic Acids Research 18(13): 3871–3879, (Mar. 27, 1990).

Louis, H.A., et al., Comparison of Three Members of the Cysteine–rich Protein Family Reveals Functional Conservation and Divergent Patterns of Gene Expression, JBC 272(43): 27484–27491, Oct. 24, 1997.

Melani, C., et al., Inhibition and Proliferation by c–myb Antisense Oligodeoxynucleotides in Colon Adenocarcinoma Cell Lines That Express c–myb. Cancer Research 51: 2897–2901, (Jun. 1, 1991).

Munro, M.J., et al., The Pathogenesis of Artherosclerosis: Artherogenesis and Inflammation. Laboratory Investigation 58(3): 249–261.

Pennica, D., et al., Cloning and Expression of Human Tissue–type Plasminogen Activator cDNA in *E. coli*. Nature 301: 214–221, (Jan. 20, 1983).

Ross, R., et al., The Pathogenesis of Artherosclerosis: a Perspective for the 1990's. Nature 362: 801–809, (Apr. 29, 1993).

Sadler, I., et al., Zyxin and cCRP: Two Interactive LIM Protein Domain Proteins Associated with the Cytoskeleton. JBC 199(6): 1573–1587, (Dec. 1992).

Tsai, J–C., et al., Promotion of Vascular Smooth Muscle Cell Growth by Homocysteine: A Link to Atroscelerosis. PNAS USA 91: 6369–6373, (Jul. 1994).

Tsai, J–C., et al., Induction of Cyclin A Gene Expression by Homocysteine in Vascular Smooth Muscle Cells. J. Clin. Invest. 97: 146–153, (Jan. 1996).

Wang, X., et al., Analysis of the Human Cysteine–rich Protein Gene (CSRP), Assignment ot Chromosome 1q24–1q32, and Identification of an Associated Msp1 Polymorphism. Genomics 14: 391–397, (Jul. 10, 1992).

Wang, X., et al., Human Cysteine–rich Protein. JBC 267(13): 9176–9184, (May 5, 1992).

Warren, A. J., et al., The Oncogenic Cysteine–rich LIM Domain Protein Rbtn2 Is Essential for Erythroid Development. Cell 78: 45–57, (Jul. 15, 1994).

Weiskirchen, R., et al., The Cysteine–rich Protein Family of Highly Related LIM Domain Proteins. JBC 270(48): 28946–28954, (Dec. 1, 1995).

Wiesel, P.,et al., Two–Kidney, One Clip and One–Kidney, One Clip Hypertension in Mice, Hypertension 29(4): 1025–1030, (Apr. 1997).

Williams, R.S., et al., Introduction of Foreign Genes into Tissues of Living Mice by DNA–coated Microprojectiles. PNAS USA 88: 2726–2730, (Apr. 1991).

Yet, S–W., et al., Molecular Cloning, Characterization, and Promoter Analysis of the Mouse Crp2/SmLim Gene. JBC 273(17): 10530–10537, (Apr. 24, 1998).

International Search Report for PCT/US97/04190.

* cited by examiner

```
-438  TGAGGAATGCAGCTCTTTCGCGACAGGAAAGCTGCGGATTCCAGAAGCCGGGATTCTGAC
                                      CACCC-box       E-box
-378  CAGAGACTATCCTGCACCGGGGAGTCCTGCACCCCGGAGGCTAACATATGGCGTTTGTGC
           CACCC-box/Sp1/NFκB
-318  AGTAAAGGGTGGCGGGAATCCCACGGGGCGACACCGGATCTCGCTGGCTCCGGGCCGATC
                                            C/EBP
-258  CTGAGTGCTCCGGACGTCCCGGACCGCGGGTAGGAGCAGCCGAGACGTGGGAGACTCGG
                                       Sp1
-198  ACGCGCGGGAAGCCGCAGGAAGAGGCGGGATTCCGGTCTTTTGTCTCGGGGCCAGAGCTC
                                 Sp1                     CACCC-box
-138  GAAACCCGCAGCGGGAGCCCCAGCTCAGCGGGCCGGGCGGAGACCATCGCACACCCCGAG
                    Sp1            Sp1
 -78  GGGCATGACCGATGATGGGCGTGGCGAACAAGGCCACGCCCAACATAAGTCTTTAAAAGC
                         ↱       Sp1/AP2
 -18  GGGCACACGCGTCCCGCCAGTCTCCGGATCCGCCCGCGGCTTTCCTCGGTCAGACCTCGT
         Sp1/AP2                       CACCC-box
 +43  TAGCTCCGCCCGCCGCGTGCTCCCTCCTCCCACTCGGgtgagtcctaggctc SEQ ID NO:16
```

Fig. 9

METHODS OF TREATING HYPERTENSION

CROSS REFERENCE TO RELATED APPLICATIONS

This application is a continuation-in-part of U.S. patent application Ser. No. 08/818,655, filed on Mar. 14, 1997, now U.S. Pat. No. 6,258,557 the contents of which is hereby incorporated by reference.

STATEMENT AS TO FEDERALLY SPONSORED RESEARCH

This invention was made with U.S. Government support under National Institutes of Health grants HL57977. The government has certain rights in the invention.

BACKGROUND OF THE INVENTION

The invention relates to hypertension.

In their normal state, vascular smooth muscle cells regulate vessel tone and blood pressure. Unlike skeletal muscle and cardiac muscle cells, these cells are not terminally differentiated. In response to mechanical, chemical, or immunologic injury (Libby et al., 1991, Lab Invest. 64:5–15; Munro et al., 1988, Lab Invest. 58:249–261; Ross, R., 1993, Nature 362:801–809; Tsai et al., 1994, Proc. Natl. Acad. Sci. USA 91:6369–6373; and Tsai et al., 1996, Clin. Invest. 97:146–153), the phenotype of these cells changes rapidly from that of a differentiated, quiescent cell to that of a dedifferentiated, proliferating cell.

SUMMARY OF THE INVENTION

The invention is based on the identification and characterization of a smooth muscle cell LIM (SmLIM/CRP2) polypeptide which is expressed preferentially in arterial smooth muscle cells. Mammals which are SmLIM-deficient are resistant to developing hypertension. Accordingly, the invention features a method of inhibiting hypertension in a mammal by identifying a mammal suffering from or at risk of developing hypertension and administering to the mammal, e.g., a human patient, a compound that reduces expression of SmLIM. An inhibitory compound inhibits transcription of SmLIM-encoding DNA or translation of an endogenous SmLIM transcript into a SmLIM gene product. For example, to inhibit SmLIM transcription, a compound which binds to a cis-acting regulatory sequence of a SmLIM gene is administered. The cis-acting regulatory sequence is located 5' to the transcription start site of SmLIM and comprises CANNTG (SEQ ID NO:44), GGGRNTYYC (SEQ ID NO:45), or CACCC (SEQ ID NO:46). The cis-acting regulatory sequence has SmLIM promoter activity and is at least at least 50% identical to SEQ ID NO:3 or 16. Preferably, the regulatory sequence comprises SEQ ID NO:3 or 16.

A compound which inhibits SmLIM transcription is preferably an antisense nucleic acid. For example, the antisense nucleic acid molecule contains at least 10 nucleotides the sequence of which is complementary to an mRNA encoding a SmLIM polypeptide. The antisense nucleic acid is a DNA operatively linked to a smooth muscle cell-specific promoter, and transcription of the DNA yields nucleic acid product which is complementary to an mRNA encoding a SmLIM polypeptide. The cell-specific promoter is preferably at least 50% identical to SEQ ID NO:3 or 16. Most preferably, the promoter contains the nucleic acid sequence of SEQ ID NO:3 or 16.

A DNA construct for production of antisense nucleic acids in a target cell is also within the invention. For example, the invention includes a substantially pure DNA containing a first DNA sequence at least 50% identical to SEQ ID NO:3 or 16, operably linked to a second DNA sequence which is an antisense template, the transcript of which is complementary to a portion of an mRNA encoding a vascular smooth muscle cell polypeptide. The first DNA sequence directs transcription of the second DNA sequence preferentially in a vascular smooth muscle cell compared to in a non-vascular smooth muscle cell. For inhibition of hypertension, the vascular smooth muscle cell polypeptide is SmLIM.

In addition to inhibiting SmLIM transcription, hypertension is reduced by inhibiting SmLIM activity. For example, a compound which inhibits SmLIM activity is a polypeptide that binds to a LIM domain. Preferably, the compound inhibits contraction of smooth muscle cells. The compound inhibits dimerization of SmLIM. Inhibitory compounds include SmLIM-specific antibodies such as an antibody which binds to an epitope comprising the amino acid sequence of residues 91–98 of SEQ ID NO:13. Intrabodies with the same specificity as SmLIM-binding antibodies are expressed intracellularly to inhibit SmLIM dimerization or to inhibit SmLIM binding to an intracellular ligand. Preferably the compound is introduced into an artery of the mammal such as a human patient.

The invention also includes a transgenic non-human mammal the germ cells and somatic cells of which comprise a null mutation in a gene encoding SmLIM. The null mutation is a deletion of part or all of an exon, e.g., exon 3. Preferably, the mammal is a rodent such as a mouse.

Methods of screening for compounds that inhibit SmLIM expression or function are also encompassed by the invention. For example, a method of screening candidate compounds to identify a compound capable of decreasing expression of SmLIM/CRP2 in vascular smooth muscle cells is carried out by (a) providing a vascular smooth muscle cell; (b) contacting the vascular smooth muscle cell with a candidate compound; and (c) determining the amount of SmLIM/CRP2 expression in the vascular smooth muscle cell. A decrease in the amount of expression, e.g, as measured by detecting SmLIM transcripts or gene products in the cell, in the presence of the candidate compound compared to the amount in the absence of the candidate compound indicates that the candidate compound decreases expression of SmLIM/CRP2 in vascular smooth muscle cells, and thus, inhibits hypertension.

The invention features a substantially pure DNA containing a sequence which encodes a SmLIM/CRP2 polypeptide. By the term "SmLIM/CRP2" is meant a polypeptide that contains at least two LIM domains, lacks a homeobox domain and a protein kinase domain, and inhibits proliferation of vascular smooth muscle cells. By "substantially pure DNA" is meant DNA that is free of the genes which, in the naturally-occurring genome of the organism from which the DNA of the invention is derived, flank the SmLIM/CRP2 gene. The term therefore includes, for example, a recombinant DNA which is incorporated into a vector, into an autonomously replicating plasmid or virus, or into the genomic DNA of a procaryote or eucaryote at a site other than its natural site; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence. A "LIM domain" is defined by the amino acid consensus sequence $CX_2CX_{17\pm1}HX_2CX_2CX_2CX_{17\pm1}CX_2C/D/H$ (SEQ ID NO:18).

The SmLIM/CRP2 polypeptide of the invention preferably has at least 85% sequence identity with SEQ ID NO:1, and more preferably at least 90% (e.g., at least 95%). The DNA may encode a naturally occurring mammalian SmLIM/CRP2 polypeptide such as a human, rat, mouse, guinea pig, hamster, dog, cat, pig, cow, goat, sheep, horse, monkey, or ape SmLIM/CRP2. For example, the SmLIM/CRP2 polypeptide may have the amino acid sequence of the naturally-occurring human polypeptide, e.g., a polypeptide which includes the amino acid sequence of SEQ ID NO:1. Preferably, the DNA includes the nucleotide sequence of SEQ ID NO:2. The DNA may contain a strand which hybridizes at high stringency to a DNA probe having a portion or all of the nucleotide sequence of SEQ ID NO:2, or the complement thereof. The probe to which the DNA of the invention hybridizes preferably consists of at least 20 nucleotides, more preferably 40 nucleotides, even more preferably 50 nucleotides, and most preferably 100 nucleotides or more (up to 100%) of the nucleotide sequence of SEQ ID NO:2, or the complement thereof. Such a probe is useful for detecting expression of a SmLIM/CRP2 transcript in a cell by a method which includes the steps of (a) contacting mRNA obtained from the cell with the labeled hybridization probe; and (b) detecting hybridization of the probe with the mRNA transcript. The invention also includes a substantially pure strand of DNA containing at least 15 nucleotides (preferably 20, more preferably 30, even more preferably 50, and most preferably all) of SEQ ID NO:2.

Hybridization is carried out using standard techniques such as those described in Ausubel et al., *Current Protocols in Molecular Biology*, John Wiley & Sons, (1989). "High stringency" refers to DNA hybridization and wash conditions characterized by high temperature and low salt concentration, e.g., wash conditions of 650C at a salt concentration of approximately 0.1×SSC. "Low" to "moderate" stringency refers to DNA hybridization and wash conditions characterized by low temperature and high salt concentration, e.g. wash conditions of less than 60° C. at a salt concentration of at least 1.0×SSC. For example, high stringency conditions may include hybridization at about 42° C., and about 50% formamide; a first wash at about 65° C., about 2 ×SSC, and 1% SDS; followed by a second wash at about 65° C. and about 0.1%×SSC. Lower stringency conditions suitable for detecting DNA sequences having about 50% sequence identity to a SmLIM/CRP2 gene are detected by, for example, hybridization at about 42° C. in the absence of formamide; a first wash at about 42° C., about 6×SSC, and about 1% SDS; and a second wash at about 50° C., about 6×SSC, and about 1% SDS.

The invention also includes a substantially pure DNA encoding a SmLIM/CRP2 polypeptide, which DNA includes a nucleotide sequence having at least 50% sequence identity to SEQ ID NO:2. Preferably the DNA has at least 70%, more preferably at least 80%, more preferably at least 90%, more preferably at least 95%, and most preferably at least 99% identity to SEQ ID NO:2. Where a particular polypeptide or nucleic acid molecule is said to have a specific percent identity or conservation to a reference polypeptide or nucleic acid molecule, the percent identity or conservation is determined by the algorithm of Myers and Miller, CABIOS (1989), which is embodied in the ALIGN program (version 2.0), or its equivalent, using a gap length penalty of 12 and a gap penalty of 4 where such parameters are required. All other parameters are set to their default positions. Access to ALIGN is readily available. See, e.g., http://www2.igh.cnrs.fr/bin/align-guess.cgi on the Internet.

The DNA may be operably linked to regulatory sequences, e.g., a promoter, for expression of the polypeptide. Preferably, the promoter is vascular cell-specific, more preferably, it is vascular smooth muscle cell-specific, and most preferably, it is arterial smooth muscle cell-specific. By "operably linked" is meant that a coding sequence and a regulatory sequence(s) are connected in such a way as to permit gene expression when the appropriate molecules (e.g., transcriptional activator proteins) are bound to the regulatory sequence(s). By "promoter" is meant a minimal DNA sequence sufficient to direct transcription. Promoters may be constitutive or inducible.

The invention includes a substantially pure DNA containing a sequence at least 50% identical to SEQ ID NO:3 or SEQ ID NO:16, which regulates arterial smooth muscle cell-specific transcription of a polypeptide-encoding sequence to which it is operably linked. Preferably, the DNA is at least 75% identical, more preferably at least 90% identical, more preferably at least 95%, and most preferably 100% identical to SEQ ID NO:3 or SEQ ID NO:16. The DNA may be operably linked to a heterologous polypeptide-encoding sequence and may be used in a method of directing arterial smooth muscle cell-specific expression of the polypeptide, e.g., by introducing the DNA linked to the coding sequence into an arterial cell. By the term "heterologous polypeptide" is meant a polypeptide other than a SmLIM/CRP2 polypeptide.

The invention also includes a substantially pure DNA comprising a first DNA sequence containing a SmLIM/CRP2-derived promoter sequence, e.g., one which is at least 50% identical to SEQ ID NO:3 or 16, operably linked to a second DNA sequence encoding a polypeptide other than SmLIM/CRP2, i.e., a heterlogous peptide, wherein the first DNA sequence directs transcription of the second DNA sequence preferentially in an a vascular smooth muscle cell, e.g., an arterial smooth muscle cell, compared to in a non-vascular smooth muscle cell. Preferably, the second DNA sequence does not encode SmLIM/CRP2. Vascular smooth muscle cell-specific expression of a polypeptide is accomplished by introducing into an vascular smooth muscle cell a vector containing SmLIM promoter sequences operably linked to polypeptide-encoding DNA and maintaining the cell under conditions suitable for expression of the second DNA, e.g., in vitro culture under standard tissue culture conditions or in vivo, i.e., in an animal. For example, the invention provides a method of inhibiting arteriosclerosis in an animal by contacting an artery of an animal with the vector containing DNA encoding a polypeptide which reduces or prevents the development of arteriosclerosis. e.g., a polypeptide which reduces proliferation of smooth muscle cells. Alternatively, the second DNA sequence may be a an antisense template the transcript of which is complementary to a portion of an mRNA encoding a vascular smooth muscle cell polypeptide. As described above, the invention includes a substantially pure DNA comprising a first DNA sequence containing a SmLIM/CRP2-derived promoter sequence, e.g, one which is at least 50% identical to SEQ ID NO:3 or 16, operably linked to a second DNA sequence which is an antisense template the transcript of which is complementary to a portion of an mRNA encoding an vascular smooth muscle cell polypeptide. The first DNA sequence directs transcription of the second DNA sequence preferentially in a vascular smooth muscle cell compared to in a non-vascular smooth muscle cell. By the term "antisense template" is meant a DNA which is transcribed into an RNA which hybridizes to mRNA encoding a polypeptide expressed in vascular smooth muscle cells.

Preferably the level of transcription of a polypeptide-encoding or antisense template in vascular smooth muscle cells under the control of a SmLIM/CRP2-derived promoter sequence is at least 2-fold greater, more preferably 3-fold, more preferably 4-fold, and more preferably 10-fold greater than that in non-vascular smooth muscle cells. Most preferably, the SmLIM/CRP2-derived promoter sequence of the invention direct vascular smooth muscle cell-specific transcription of the DNA to which it is linked.

The invention also includes a vector containing the promoter sequences of the invention, a method of directing vascular smooth muscle cell-specific expression of a polypeptide by introducing the vector into an vascular smooth muscle cell, and a vascular smooth muscle cell containing the vector.

The vector of the invention can be used for gene therapy, such as a method of inhibiting arteriosclerosis in an animal by contacting an artery of the animal with the vector of the invention which directs the production of a polypeptide capable of reducing or preventing the development of arteriosclerosis.

A cell which contains a recombinant SmLIM/CRP2 polypeptide-encoding DNA is also within the invention. The cell may be eucaryotic or procaryotic. A method of making a SmLIM/CRP2 polypeptide includes the steps of (a) providing the cell which contains SmLIM/CRP2 polypeptide-encoding DNA, and (b) culturing it under conditions permitting expression of the DNA. If the polypeptide is secreted by the cell, the SmLIM/CRP2 polypeptide produced can be recovered from the culture supernatant of the cell culture. If the polypeptide is not secreted, the polypeptide can be recovered by lysing the cultured cells.

The invention also includes a substantially pure human SmLIM/CRP2 polypeptide. Preferably, the amino acid sequence of the polypeptide is at least 90% identical, more preferably at least 95% identical, more preferably at least 99% identical to the amino acid sequence of SEQ ID NO:1. Most preferably, the amino acid sequence of the polypeptide includes SEQ ID NO:1. By a "substantially pure polypeptide" is meant a polypeptide which is separated from those components (proteins and other naturally-occurring organic molecules) which naturally accompany it. Typically, the polypeptide is substantially pure when it constitutes at least 60%, by weight, of the protein in the preparation. Preferably, the protein in the preparation consists of at least 75%, more preferably at least 90%, and most preferably at least 99%, by weight, a SmLIM/CRP2 polypeptide. A substantially pure SmLIM/CRP2 polypeptide may be obtained, for example, by extraction from a natural source (e.g., an arterial smooth muscle cell); by expression of a recombinant nucleic acid encoding a SmLIM/CRP2 polypeptide; or by chemically synthesizing the protein. Purity can be measured by any appropriate method, e.g., column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components even without further purification steps. Accordingly, substantially pure polypeptides include recombinant polypeptides derived from a eucaryote but produced in E. coli or another procaryote, or in a eucaryote other than that from which the polypeptide was originally derived.

The invention also includes diagnostic methods. SmLIM/CRP2 expression was found to decrease as vascular smooth muscle cells changed from a quiescent, differentiated phenotype to a proliferative phenotype in response to vascular injury. One can detect injury in a sample of vascular tissue by determining the level of SmLIM/CRP2 gene expression in the tissue sample, and comparing it to the level of expression in a control sample of vascular tissue. This determination may be made using SmLIM/CRP2-specific DNA probes to detect the level of gene transcription or using SmLIM/CRP2-specific antibodies to detect the level of gene product in the cells. A decrease in the level of expression of SmLIM/CRP2 compared to the level in uninjured control vascular tissue indicates the presence of a vascular injury.

Methods of therapy are also within the invention. A method of inhibiting arterial smooth muscle cell proliferation in a mammal may include the steps of identifying a mammal in need of such inhibition, and introducing either SmLIM/CRP2 or a SmLIM/CRP2-encoding DNA into an artery of the mammal. One can inhibit neointima formation after balloon angioplasty in a mammal by contacting an artery of the mammal with a SmLIM/CRP2 or SmLIM/CRP2-encoding DNA prior to, during, or immediately after angioplasty to reduce proliferation of arterial smooth muscle cells in the mammal, particularly at the site of vascular injury treated by the angioplasty procedure. Preferably, the mammal is a human, and the SmLIM/CRP2 polypeptide is a human SmLIM/CRP2 polypeptide.

A method of screening candidate compounds to identify a compound capable of increasing expression of a SmLIM/CRP2 polypeptide in vascular smooth muscle cells is also within the invention. For example, an in vitro method may include the steps of (a) providing a vascular smooth muscle cell, e.g., a human arterial smooth muscle cell; (b) contacting the smooth muscle cell with a candidate compound; and (c) determining the amount of SmLIM/CRP2 expression by the vascular smooth muscle cell. The screening method can also be carried out in vivo, e.g., in an animal subjected to a vascular injury, and then treated with the candidate compound or a placebo. An increase in the amount of expression in the presence of the candidate compound compared to that in the absence of the candidate compound indicates that the candidate compound increases expression of a SmLIM/CRP2 polypeptide in vascular smooth muscle cells. An increase of SmLIM/CRP2 expression correlates with an inhibition in vascular smooth muscle cell proliferation. Expression may be determined by measuring gene transcription, e.g., in a Northern blot assay, or by measuring the amount of SmLIM/CRP2 polypeptide in the cell, e.g., by immunoblotting.

Other features and advantages of the invention will be apparent from the following detailed description, and from the claims.

BRIEF DESCRIPTION OF THE DRAWINGS

FIG. 9 is a diagram of a SmLIM-CRP2 promoter sequence (SEQ ID NO:16) in which cis-acting transcriptional regulatory sequences are indicated above the DNA sequence. The DNA sequence is numbered on the left. Cis-acting sequences are underlined. A TATA-like sequence is in boldface. The transcriptional start site is marked by a bent arrow, and intron 1 sequences are in lower case.

DETAILED DESCRIPTION

Cell Culture and Reagents

Figure 1:
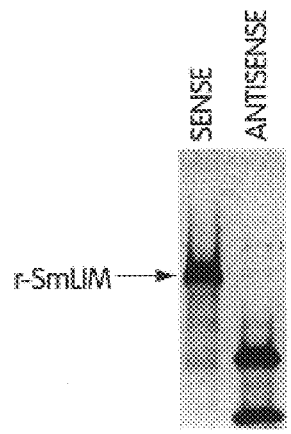
FIG. 1 is a photograph of an sodium dodecyl sulfate-polyacrylamide gel electrophoresis (SDS-PAGE) analysis of proteins. The entire rat (r-SmLIM/CRP2) open reading frame was cloned in the sense and antisense orientations into the eucaryotic expression vector PCRIII. After in vitro transcription and translation with wheat germ lysate, the protein was resolved on a 10% SDS-PAGE Tricine gel. The single intense band in the sense lane (arrow) represents full-length SmLIM/CRP2 at 21 kDa.

Aortic smooth muscle cells were harvested from the thoracic aorta of adult male Sprague-Dawley rats (200–250 g) by enzymatic digestion. COS-7 (CRL 1651) and 10T1/2 (CCL 226) cells were obtained from the American Type Cell Culture Collection. Rat aortic smooth muscle cells were grown in DME medium (JRH Biosciences, Lenexa, Kans.) supplemented with 10% FCS, penicillin (100 U/ml), streptomycin (100 µg/ml), and 25 mM Hepes (pH 7.4) in a humidified incubator (37° C., 5% $CO_2$). COS-7 and 10T1/2 cells were grown similarly, with the exceptions that DME was supplemented with Serum Plus (Hyclone, Logan, Utah) for the former and BME (JRH Biosciences) was substituted for DME for the latter. Embryonic stem cells (D3) were cultured using known methods. Cells were cultured and maintained in an undifferentiated state with leukemia inhibitory factor using known methods, e.g., Doetschman et al., 1985, J. Embryol. Exp. Morph. 87:27–45. PDGF-BB was purchased from Collaborative Biomedical Products (Bedford, Mass.).

Cloning and Sequencing of r-SmLIM/CRP2, Mouse SmLIM/CRP2 (m-SmLIM/CRP2) and h-SmLIM/CRP2

The full-length rat muscle LIM protein (MLP) cDNA was amplified from rat heart RNA by the reverse transcriptase PCR. Forward (5'GAGTCTTCACCATGCCGAAC3' SEQ ID NO:4) and reverse (5'CTCTCCCACCCCAAAAATAG3' SEQ ID NO:5) primers, designed according to the published rat MLP sequence (Arber et al., 1994, Cell 79:221–231), were used to amplify a 801-bp fragment. The PCR fragment was then subcloned and sequenced by the dideoxy chain termination method. The rat-MLP fragment was used to screen a rat neonatal aortic cDNA library in λ.gt11. Approximately 1.6 million phage clones were plated, transferred to nitrocellulose paper, and screened at low stringency. One out of nine isolated clones encoded the partial sequence of a novel LIM protein, r-SmLIM/CRP2. This partial clone was then used to screen a rat smooth muscle cDNA library in λZAP (Clontech) to obtain the full-length clone. The same partial rat clone was also used to screen a human aortic λ.gt11 cDNA library to obtain the human sequence and a murine library to obtain the murine sequence. The sequences of several partially overlapping clones were compiled to obtain the full-length h-SmLIM/CRP2 sequence. Both strands of the entire r-SmLIM/CRP2 and h-SmLIM/CRP2 cDNAs were sequenced by the dideoxy chain termination method or on an automated DNA Sequencer (Licor, Lincoln, Nebr.) according to the manufacturer's instructions.

The nucleotide sequences have been submitted to the GENBANK™/EMBL Data Bank with accession numbers U44948 (r-SmLIM/CRP2) and U46006 (h-SmLIM/CRP2).

Cellular Localization of r-SmLIM/CRP2

To construct the expression plasmid Myc-SmLIM/CRP2/pCR3, DNA encoding a c-Myc peptide tag (EQKLISEED; SEQ ID NO:6) was added in frame to the r-SmLIM/CRP2 open reading frame at the N-terminus using PCR techniques. This hybrid DNA fragment was then cloned into the eucaryotic expression vector pCR3 (Invitrogen). COS-7 and 10T1/2 cells were transiently transfected with the Myc-SmLIM/CRP2/pCR3 plasmid using the DEAE-dextran method known in the art. The transfected cells were grown on chamber slides and fixed with 4% paraformaldehyde in PBS. Immunostaining was performed 48 h after transfection with an anti-c-Myc monoclonal antibody (e.g., 9E10; Oncogene) followed by a rhodamine-conjugated goat anti-mouse IgG secondary antibody. Nuclear counterstaining was performed with Hoechst 33258 according to the manufacturer's instructions.

Chromosomal Localization of h-SmLIM/CRP2

The chromosomal location of h-SmLIM/CRP2 was determined using the BIOSMAP Somatic Cell Hybrid blot (BIOS Laboratories, Conn.), which contains DNA from 20 somatic cell hybrid cell lines plus 3 control DNAs (human, hamster, and mouse). A full-length h-SmLIM/CRP2 fragment was randomly primed and hybridized as recommended by the manufacturer. The blot was washed according to the manufacturer's instructions and then exposed to Kodak XAR film at −80° C.

RNA Extraction and RNA Blot Analysis

Total RNA was isolated from cultured cells, rat organs, embryonic stem cells, and mouse embryos by guanidinium isothiocyanate extraction and centrifugation through cesium chloride. The mouse embryo samples (7–10 days old) included placenta and yolk sac tissue. Carotid artery total RNA was obtained by the RNA-Zol method (Cinna/Biotecx Laboratories International, Houston, Tex.) from adult male Sprague-Dawley rats that had been subjected to balloon injury (Zivic-Miller Company, Zelienople, Pa.). Human poly $A^+$ RNA was purchased from Clontech Laboratories (Palo Alto, Inc. Calif.). All RNA was fractionated on a 1.3% formaldehyde-agarose gel and transferred to nitrocellulose filters. The filters were then hybridized with the appropriate $^{32}$P-labeled, random primed cDNA probes using standard methods. The hybridized filters were washed in 30 mM sodium chloride, 3 mM sodium citrate, and 0.1% SDS at 55° C. and autoradiographed on Kodak XAR film at −80° C. To control for differences in RNA loading, the blots were hybridized with an 18S-specific or 28S-specific oligonucleotide probe. The filters were scanned and radioactivity was measured on a PhosphorImager running the ImageQuant software (Molecular Dynamics, Sunnyvale, Calif.).

In vitro Transcription and Translation

The complete r-SmLIM/CRP2 open reading frame was cloned into the eucaryotic expression vector pCR3 (Invitrogen). In vitro transcription and translation was performed in the TNT-coupled wheat germ extract system (Promega, Madison, Wis.) according to the manufacturer's instructions. The transcribed and translated products were resolved on a 10% SDS-PAGE Tricine gel, and autoradiography was performed with Kodak BMR film at room temperature.

In situ Hybridization

Rat SmLIM/CRP2 mRNA was hybridized in situ using standard methods. Adult male Sprague-Dawley rats were perfused with 4% paraformaldehyde. Organs were then postfixed with 4% paraformaldehyde, soaked in 30% sucrose until the tissue sank, embedded in optimum cutting temperature (O.C.T.) compound, and stored in isopentane at −80° C. Tissue sections were cut at a thickness of 5 microns. SmLIM/CRP2 mRNA was detected by hybridization with a [$^{35}$S]UTP-labeled antisense cRNA probe synthesized with the SP6 RNA polymerase from HindIII-linearized r-SmLIM/CRP2 in Bluescript II SK+. For control experiments, a [$^{35}$S]UTP-labeled sense cRNA probe was synthesized under the same conditions. RNA probes were degraded to a length of approximately 100–200 nucleotides by partial hydrolysis for 15 min at 60° C. in 80 mM $NaHCO_3$ and 120 mM $Na_2CO_3$. After hybridization, the tissue sections were washed under moderately stringent conditions (Lee et al., 1993, Endocrinology 132:2136–2140). The dried tissue sections were then dipped into Kodak NTB2 emulsion (Eastman Kodak, Rochester, N.Y.) and exposed for 2–4 days at 4° C. Counterstaining was performed with hematoxylin-eosin.

Isolation and Characterization of r-SmLIM/CRP2 and h-SmLIM/CRP2 cDNA

The nucleotide sequence of the r-SmLIM/CRP2 cDNA revealed a 582-bp open reading frame encoding a 194 amino-acid protein. Analysis of this frame identified two LIM domains separated by a glycine-rich region and a putative nuclear localization signal.

TABLE 1 shows the complete nucleotide (upper line) and deduced amino acid (lower line) sequences of r-SmLIM/CRP2. Residues composing the two LIM domains are in boldface, a putative nuclear localization signal is underlined, and the polyadenylation signal is underlined and in italics. The nucleotide sequence flanking the putative initiation methionine complied with the Kozak consensus sequence for initiation of translation. A 21 kDa polypeptide was encoded by the r-SmLIM/CRP2 open reading frame.

The entire r-SmLIM/CRP2 cDNA was cloned into the PCRIII eucaryotic expression vector. In vitro transcription and translation (Promega) of this expression plasmid with wheat germ lysate revealed a protein product of 21-kDa (FIG. 1).

Conservation of SmLIM/CRP2 Among Species

To determine whether SmLIM/CRP2 was conserved across species, the human, rat, and mouse homologues were compared. A comparison of the h-SmLIM/CRP2 and r-SmLIM/CRP2 open reading frames revealed 93% identity at the cDNA level and 99% identity at the amino acid level (TABLES 2 AND 3). Comparison of the open reading frames of murine SmLIM/CRP2 (m-SmLIM/CRP2) and r-SmLIM/CRP2 revealed 97% identity at the cDNA level and 100% identity at the amino acid level (TABLE 3). A GENBANK™ search indicated that SmLIM/CRP2 shares homology with the cysteine-rich protein (CRP) family, a characteristic reflected in the name of this novel polypeptide. TABLE 2 compares r-SmLIM/CRP2 and h-SmLIM/CRP2 with their rat and human CRP counterparts and rat MLP. Although an amino acid sequence comparison of r-SmLIM/CRP2 and h-SmLIM/CRP2 shows 99% identity (TABLE 3), a comparison of r-SmLIM/CRP2 with r-CRP shows only 79% identity. These data indicate that SmLIM/CRP2 and CRP are related but different genes.

TABLE 2 shows a sequence alignment of rat (r)-SmLIM/CRP2 and human (h)-SmLIM/CRP2 proteins to the LIM proteins r-CRP, h-CRP, and r-MLP. Consensus sequence indicates residues conserved in all five proteins. Cysteine and histidine residues composing LIM domains are underlined.

TABLE 1

```
  1 ACGAGCTAGACCTCCCTAGCTCCGCCCGCCGCGTGCTCCCGCCTCCCACTCGGAATGCCT
                                                             M  P

61 GTCTGGGGCGGTGGAAATAAGTGCGGGGCCTGCGGGAGAACCGTGTACCACGCTGAAGAG
     V  W  G  G  G  N  K  C  G  A  C  G  R  T  V  Y  H  A  E  E

121 GTGCAGTGTGATGGGCGGACGTTCCACCGCTGCTGCTTTCTGTGCATGGTTTGCAGGAAA
     V  Q  C  D  G  R  T  F  H  R  C  C  F  L  C  M  V  C  R  K

181 AATTTAGACAGCACAACAGTGGCAATTCATGATGAAGAGATCTACTGCAAATCATGCTAC
     N  L  D  S  T  T  V  A  I  H  D  E  E  I  Y  C  K  S  C  Y

241 GGAAAGAAGTATGGACCAAAAGGCTATGGTTATGGCCAGGGCGCTGGCACGCTCAACATG
     G  K  K  Y  G  P  K  G  Y  G  Y  G  Q  G  A  G  T  L  N  M

301 GACCGTGGTGAGAGGCTGGGCATCAAGCCAGAGAGTGCTCAACCTCACAGGCCTACAACA
     D  R  G  E  R  L  G  I  K  P  E  S  A  Q  P  H  R  P  T  T

361 AATCCAAACACTTCTAAATTTGCCCAGAAATATGGAGGTGCTGAGAAGTGCTCCAGATGT
     N  P  N  T  S  K  F  A  Q  K  Y  G  G  A  E  K  C  S  R  C

421 GGGGATTCTGTGTATGCTGCTGAGAAGATCATTGGAGCTGGAAAGCCCTGGCACAAAAAC
     G  D  S  V  Y  A  A  E  K  I  I  G  A  G  K  P  W  H  K  N

481 TGTTTCCGATGTGCCAAGTGTGGGAAGAGTCTGGAGTCTACAACTCTGACTGAGAAGGAA
     C  F  R  C  A  K  C  G  K  S  L  E  S  T  T  L  T  E  K  E

541 GGTGAAATCTACTGTAAAGGGTGCTACGCAAAGAACTTTGGGCCCAAGGGATTCGGCTAT
     G  E  I  Y  C  K  G  C  Y  A  K  N  F  G  P  K  G  F  G  Y

601 GGTCAAGGAGCAGGGGCCCTTGTTCATGCTCAGTAGTGGTGTAAACCCAGTAAGCATGGC
     G  Q  G  A  G  A  L  V  H  A  Q  *  (SEQ ID NO: 8)

661 AAAGAACCTCCATTAATGTGGATGGCCTTACCGCACTCAGGCTGTGCATCGGCCAGCACT

721 CAGCACTGTGTAGCACACACGCTATGTGCACAATCGGGCTGGACAGGAAGCACTACACTC

781 TCCTGCCCATCCGCTAACGTTTAAGAACGTTCTTTTACATTTGGAATAAAATTTTGGTTT

841 GATTTGAAAAAAAAAAAAAAAAAAAAAAAAAAAAAAAAAA (SEQ ID NO: 7)
```

TABLE 2

```
              1         .         .         .         .        50
   r-SmLIM   MPVWGGGNKCGACGRTVYHAEEVQCDGRTFHRCCFLCMVCRKNLDSTTVA
   h-SmLIM   MPVWGGGNKCGACGRTVYHAEEVQCDGRSFHRCCFLCMVCRKNLDSTTVA
     r-CRP   MPNWGGGKKCGVCQKTVYFAEEVQCEGNSFHKSCFLCMVCKKNLDSTTVA
     h-CRP   MPNWGGGKKCGVCQKTVYFAEEVQCEGNSFHKSCFLCMVCKKNLDSTTVA
     r-MLP   MPNWGGGAKCGACDKTVYHAEEIQCNGRSFHKTCFHCMACRKALDSTTVA
 Consensus   MPNWGGGNKCGNCNNTVYNAEEVQCNGNNFHNNCFNCMNCNKNLDSTTVA 51        .         .         .         .       100
   r-SmLIM   IHDEEIYCKSCYGKKYGPKGYGYGQGAGTLNMDRGERLGIKPESAQPH R
   h-SmLIM   IHDEEIYCKSCYGKKYGPKGYGYGQGAGTLNMDRGERLGIKPESVQPH R
     r-CRP   VHGEEIYCKSCYGKKYGPKGYGYGQGAGTLSMDKGESLGIKHEEAPGH R
     h-CRP   VHGEEIYCKSCYGKKYGPKGYGYGQGAGTLSTDKGESLGIKHEEAPGH R
     r-MLP   AHESEIYCKVCYGRKYGPKGIGYGQGAGCLSMDTGEHLGLQFQQSPKPAR
 Consensus   NHNNEIYCKNCYGNHYGPKGNGYGQGQGNLNNDNGENLGNNNNNNNNNNR 101       .         .         .         .       150
   r-SmLIM   PTTNPNTSKFAQKYGGAEKCSRCGDSVYAAEKIIGAGKPWHKNCFRCAKC
   h-SmLIM   PTTNPNTSKFAQKYGGAEKCSRCGDSVYAAEKIIGAGKPWHKNCFRCAKC
     r-CRP   PTTNPNASKFAQKIGGAERCPRCSQAVYAAEKVIGAGKSWHKSCFRCAKC
     h-CRP   PTTNPNASKFAQKYGGAEKCSRCGDSVYAAEKIIGAGKPWHKACFRCAKC
     r-MLP   AATTSNPSKFSAKFGESEKCPRCGKSVYAAEKVMGGGKPWHKTCFPCAIC
 Consensus   NNTNNNNSKFNNKNGNNENCNRCNNNVYAAEKNNGNGKNWHKNCFNCANC 151       .         .         .         .       194
   r-SmLIM   GKSLESTTLTEKEGEIYCKGCYAKNFGPKGFGYGQGAGALVHAQ (SEQ ID NO: 8)
   h-SmLIM   GKSLESTTLTEKEGEIYCKGCYAKNFGPKGFGYGQGAGALVHAQ (SEQ ID NO: 1)
     r-CRP   GKSLESTTLADKDGEIYCKGCYAKNFGPKGFGYGQGAGALVHSE (SEQ ID NO: 9)
     h-CRP   GKSLESTTLADKDGEIYCKGCYAKNFGPKGFGYGQGAGALVHSE (SEQ ID NO: 10)
     r-MLP   GKSLESTNVTDKDGELYCKVCYAKNFGPTGIGFGGLTHQVEKKE (SEQ ID NO: 11)
 Consensus   GKNLESTNNNNKNGENYCKNCYAKNFGPNGNGNGNNNNNNNNNN (SEQ ID NO: 12)
```

TABLE 3

| r-SmLIM/CRP2 vs. | | Nucleotides (%) | Amino Acids (%) |
|---|---|---|---|
| | m-SmLIM/CRP2 | 97 | 100 |
| | h-SmLIM/CRP2 | 93 | 99 |
| | r-CRP | 73 | 79 |
| | h-CRP | 72 | 79 |
| | r-MLP | 65 | 65 |

TABLE 3 shows the percentage nucleotide and amino acid identity of r-SmLIM versus mouse m-SmLIM and h-SmLIM homologues, r-CRP, h-CRP, and r-MLP.

TABLE 4 shows the nucleotide sequence of the h-SmLIM cDNA.

TABLE 4

```
  1 ATGCCTGTCT GGGGAGGTGG AAACAAGTGT GGGGCCTGTG GAGGACCGT
 51 GTACCACGCA GAAGAGGTGC AGTGTGATGG CAGGAGCTTC CACCGCTGCT
101 GCTTTCTCTG CATGGTTTGC AGGAAAAATT TAGATAGCAC AACAGTGGCA
151 ATTCACGATG AAGAGATCTA CTGCAAATCC TGCTACGGAA AGAAGTATGG
201 GCCAAAAGGC TACGGTTATG GCCAGGGCGC TGGCACGCTt aacatggacc
251 gtggcgagag gctgggcatc aaaccagaga gtgttcagcc tcacaggcct
301 acaacaaatc caaacacttc taaatttgct cagaaatatg gaggtgctga
351 gaAGTGTTCC AGATGTGGGG ATTCTGTATA TGCTGCCGAG AAGATAATTG
401 GAGCTGGAAA GCCCTGGCAC AAAAACTGTT TCCGATGTGC AAAGTGTGGG
451 AAGAGTCTTG AATCAACAAC TCTGACTGAA AAAGAAGGTG AAATCTATTG
501 TAAAGGATGC TATGCAAAGA ACTTTGGGCC CAAGGGATTT GGCTATGGCC
551 AAGGAGCAGG GGCTCTTGTT CATGCCCAGT AAGATGTAAA CCCTGAACTA
601 AACATCACAC ACTGAGAATC TCTTCATAAT CTAGGCACAG ATAATCTTTA
651 ACCCGGAATT CCGCCGATAC TGACGGGCTC CAGGAGTCGT CGCCACCAAG
701 CCGAATTCCA GCACACTGGC GGcCGTTACT AGTGGATCCG A
   (SEQ ID NO:2)
```

TABLE 5 shows the nucleotide sequence of m-SmLIM/CRP2 cDNA and amino acid sequence of the m-SmLIM/CRP2 polypeptide.

TABLE 5

```
   AGTCTCCGGATCCGCCCGCGGCTTTCCTCGGTCAGACCTCGTTAGCTCCGCCCGCCGCGT    60

GCTCCCTCCTCCCACTCGGAATGCCTGTCTGGGGCGGTGGAAATAAGTGCGGGGCCTGCG   120
 1                      M  P  V  W  G  G  N  K  C  G  A  C  G

GGAGAACCGTGTACCACGCGGAAGAGGTGCAGTGCGATGGGCGGACGTTCCATCGCTGCT   180
15   R  T  V  Y  H  A  E  E  V  Q  C  D  G  R  T  F  H  R  C  C

GCTTCCTGTGCATGGTTTGCAGGAAAAATTTAGACAGCACAACAGTGGCGATTCATGATG   240
35   F  L  C  M  V  C  R  K  N  L  D  S  T  T  V  A  I  H  D  E

AAGAGATCTACTGCAAATCCTGCTACGGAAAGAAGTATGGACCAAAAGGCTATGGTTATG   300
55   E  I  Y  C  K  S  C  Y  G  K  K  Y  G  P  K  G  Y  G  Y  G

GCCAGGGCGCTGGCACGCTCAACATGGACCGCGGTGAGAGACTGGGCATCAAGCCAGAGA   360
75   Q  G  A  G  T  L  N  M  D  R  G  E  R  L  G  I  K  P  E  S

GTGCTCAACCTCACAGGCCTACGACAAATCCAAACACTTCTAAATTTGCCCAGAAATATG   420
95   A  Q  P  H  R  P  T  T  N  P  N  T  S  K  F  A  Q  K  Y  G

GAGGAGCTGAGAAGTGTTCCAGGTGTGGGGATTCCGTGTATGCTGCGGAGAAGATCATTG   480
115  G  A  E  K  C  S  R  C  G  D  S  V  Y  A  A  E  K  I  I  G

GAGCTGGGAAGCCCTGGCACAAAAACTGTTTCCGGTGTGCCAAGTGTGGGAAGAGTCTGG   540
135  A  G  K  P  W  H  K  N  C  F  R  C  A  K  C  G  K  S  L  E

AGTCTACAACTCTGACTGAGAAAGAAGGCGAAATCTACTGTAAAGGGTGCTACGCAAAGA   600
155  S  T  T  L  T  E  K  E  G  E  I  Y  C  K  G  C  Y  A  K  N

ACTTTGGGCCCAAGGGATTTGGCTATGGTCAAGGGGCAGGGGCCCTTGTTCATGCTCAGT   660
175  F  G  P  K  G  F  G  Y  G  Q  G  A  G  A  L  V  H  A  Q  *
                                                     (SEQ ID NO:13)

AATGGTGTGAACCAGTAAGCACGACAGAGAATCTCCATTACCAAACTGCAGATGGCGTTT   720

ATGGCGCTCACTACTGTGAAACAGCCAGCACTTGGCACTGGGCATCACCGAGCTGCCTGT   780

GGGGGCTGGACCGACAGCGCTGCACTCTCCCGCCCACTCACTAGCGTCTAAGAGCATTCT   840
                                                     (SEQ ID NO:14)
```

The number of nucleotide and amino acid sequence positions are indicated in the right and left margins, respectively. The potential nuclear localization signal is underlined. The conserved cysteine and histidine residues of the two LIM domains are in bold, and the adjacent glycine residues in the glycine-rich repeat are in italics.

Identification of the Transcription Start Site and Potential cis-acting Sequences The transcription start site was determined using an end-labeled SmLIM/CRP2 fragment in an S1 nuclease protection assay. Protected fragments were observed when the probe was incubated with total RNA prepared from primary culture of mouse aortic smooth muscle cells but not when the probe was incubated with tRNA or total RNA from mouse skeletal muscle. The transcription start site was determined to be 80 bp 5' of the translation initiation codon and it corresponds to an A nucleotide, consistent with the result obtained from 5'-RACE. The 5'CA3' nucleotide pair at this site is the most common type of eukaryotic transcription start site. The transcription start site included a pyrimidine-rich sequence that is homologous but not identical to a consensus initiator repeat sequence (YAYTCYYY; SEQ ID NO:41) in that a G residue replaces the Y at +2 position. The 5'-flanking region of SmLIM/CRP2 was characterized by islands rich in G and C (FIG. 9). A TATA-like sequence (TTTAAA; SEQ ID NO:42) was located 27 bp 5' of the transcription start site. A consensus CCAAT (SEQ ID NO:43) box was not found near the transcription start site. Comparison of the 5'-flanking sequence with sequences in the Transcription Factors Data Base revealed a series of five Sp1 sites located between nucleotides −308 and −39, and two additional Sp1 sites located within the untranslated region of the first exon. One E-box/bHLH transcription factor binding site (CANNTG; SEQ ID NO:44) was located at position −334, one NFκB-binding element (GGGRNTYYC; SEQ ID NO:45) at −305, and one C/EBP binding site at bp −230. In addition, two consensus AP2 sites were found within the first exon. Finally, four CACCC (SEQ ID NO:46)-boxes were located at bp −349, −312, −87, and +78.

Analysis of the Promoter Activity of the 5'-flanking Sequence of SmLIM/CRP2

Figure 10:
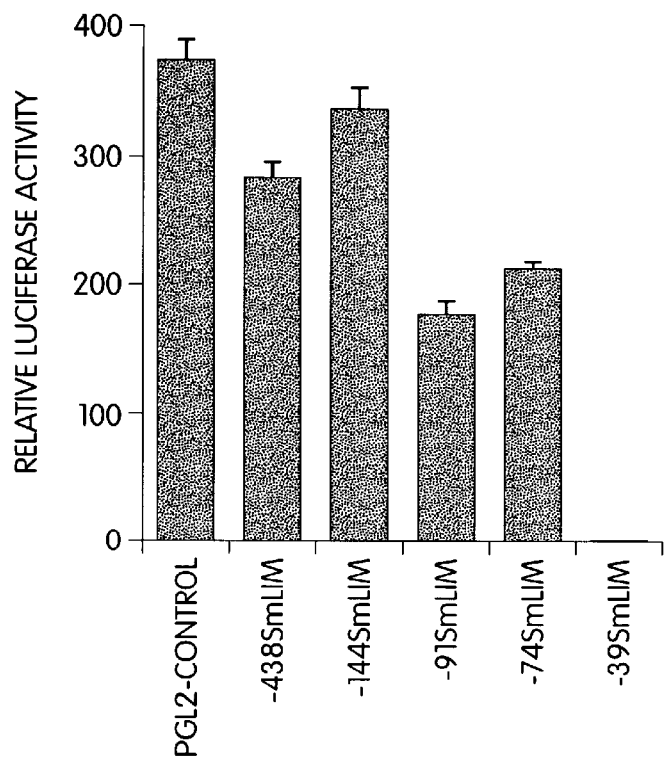
FIG. 10 is a bar graph showing the results of a functional analysis of the mouse SmLIM/CRP2 promoter. Luciferase promoter constructs containing various lengths of SmLIM/CRP2 5' flanking sequence were transfected in rat smooth muscle cells. All constructs were cotransfected with the control plasmid pOPRSVICAT to correct for transfection efficiency, and luciferase activity was expressed relative to the activity of −39SmLIM/CRP2 (mean±SEM).
Figure 11:
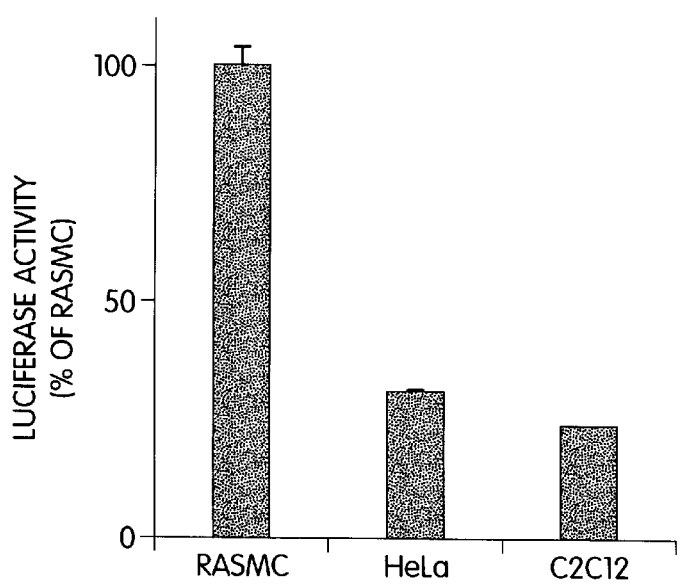
FIG. 11 is a bar graph showing SmLIM/CRP2 promoter activity in different cell types. The luciferase reporter construct −438SmLIM/CRP2 was transfected into various cell types, and luciferase activity measured. Transfection efficiency was corrected by cotransfection with pOPRSVICAT for RASMC, and pSVβgal for HeLa and C2C12 cells. Promoter activity was normalized for transfection efficiency in different cell types by comparing the activity in each cell type to the activity observed in that cell type transfected with pGL2-Control plasmid. Luciferase activity was expressed as the percentage of promoter activity in detected in RASMC. The results represent the average of three transfection experiments.

To determine whether the sequence flanking the 5' end of the SmLIM/CRP2 gene has promoter activity, the plasmid −438SmLIM/CRP2 (which contains 438 bp of the mouse SmLIM/CRP2 5'-flanking region linked to the luciferase gene) was transfected into RASMC. The control plasmid, pGL2-Control, was also transfected into RASMC. The luciferase activity generated by −438SmLIM/CRP2 was 75% that of pGL2-Control. These data indicate that the 5'-flanking region of the SmLIM/CRP2 coding sequence contains potent promoter activity. To further localize the cis-acting elements, reporter plasmids containing various lengths of SmLIM/CRP2 5'-flanking region were into RASMC (FIG. 10). As little as 74 bp of SmLIM/CRP2 promoter directed high level of promoter activity; however, a further deletion of 35 bp of promoter sequence markedly decreased the luciferase activity. These data indicate that basepairs −39 to −74 of the SmLIM/CRP2 gene contain most of the promoter activity. To determine whether the SmLIM/CRP2 promoter was active in other cell types, −438 SmLIM/CRP2 was also transfected into HeLa cells and C2C12 myoblasts. The −438SmLIM/CRP2 conferred 3- to 4-fold higher activity in RASMC than HeLa and C2C12 cells (FIG. 11).

TABLE 6 and 7 show the m-SmLIM/CRP2 promoter. In TABLE 6, the transcription start site is indicated with an arrow.

Genomic Organization of the m-SmLIM/CRP2 Gene

Figure 8:
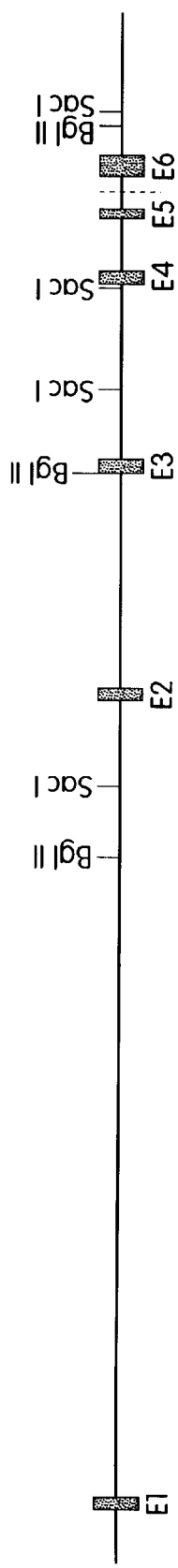
FIG. 8 is a diagram showing the structural organization and partial restriction map of the gene encoding mouse SmLIM/CRP2. Exons are shown as filled rectangles.

Using the SmLIM/CRP2 full length cDNA as a probe to screen a library prepared from mouse genomic DNA (129SvJ), several overlapping clones encoding SmLIM/CRP2 genomic sequence were isolated. The mouse SmLIM/CRP2 gene was found to be organized into six exons and five introns spanning approximately 20 kb (FIG. 8). All exon/intron boundaries were determined by DNA

TABLE 6

```
  1 TGAGGAATGC AGCTCTTtCG CGACAGGAAA GCTGCGGATT CCAGAAGCCG
 51 GGATTCTGAC CAGAGACTAT CTGCACCGGG GAGTCCTGCA CCCCGAGCTA
101 ACATATGgCG TTTGTGCAGT AAAAGGGTGG CGGGAATCCC ACGGGCGAC
151 ACCGGATCTC GCTGGCTCCG GGCCGATCCT GAGTGCTCCG GACGTCCCGG
201 GACCGCGGGT AGGAGCAGCC GAGACGTGGG AGACTCGGAC GCGGGAAGCC
251 GCAGGAAGAG GCGGATTCCG GTCTTTTTGT CTCGGGGCCA GAGCaCGAAA
301 CCCGCAtCGG ATCCCCGAGC TCACGCCGGG CGGAGACCAT CGCACACCCG
351 AGGGGCATGA CCGATGGCTG AGTCGGAACA AGCCACGCCC AACATAAGTC
                                  →
401 TTTAAAAGCG GGCACACGCG TCCCGCCAGT CTCCGGATCC GCCCGCCGGC
451 TTTCCTCGGT CAGACCTCGT TAGCTCCGCC CGCCGCGTGC TCCCTCCTCC
501 CACTCGGgtg agtcctaggc tc (SEQ ID NO:16)
```

TABLE 7

```
  1 TGAGGAATGC AGCTCTTtCG CGACAGGAAA GCTGCGGATT CCAGAAGCCG
 51 GGATTCTGAC CAGAGACTAT CTGCACCGGG GAGTCCTGCA CCCCGAGCTA
101 ACATATGgCG TTTGTGCAGT AAAAGGGTGG CGGGAATCCC ACGGGCGAC
151 ACCGGATCTC GCTGGCTCCG GGCCGATCCT GAGTGCTCCG GACGTCCCGG
201 GACCGCGGGT AGGAGCAGCC GAGACGTGGG AGACTCGGAC GCGGGAAGCC
251 GCAGGAAGAG GCGGATTCCG GTCTTTTTGT CTCGGGGCCA GAGCaCGAAA
301 CCCGCAtCGG ATCCCCGAGC TCACGCCGGG CGGAGACCAT CGCACACCCG
351 AGGGGCATGA CCGATGGCTG AGTCGGAACA AGCCACGCCC AACATAAGTC
401 TTTAAAAGCG GGCACACGCG TCCCGCC (SEQ ID NO:3)
```

Sp1 Protein Binding to the Core Promoter of SmLIM/CRP2

Using the DNA fragment encoding bp −39 to −74 (which contains two Sp1 sites) as a probe in gel-mobility-shift analysis, a specific DNA-protein complex was detected when the probe was incubated with nuclear extracts prepared from RASMC. The DNA-protein complex was deemed to be specific because a 100-fold molar excess of unlabeled identical competitor, but not a DNA fragment encoding the ATF sequence, abolished the binding complex. In addition, this DNA-protein complex was competed away by a DNA fragment containing consensus Sp1 oligonucleotide, indicating the presence of Sp1 binding proteins in the complex. To further characterize the binding proteins, gel mobility shift assay was performed in conjunction with antibodies. Antibodies to Sp1 supershifted the upper part of the DNA-protein complex. In contrast, antibodies to AP2 had no effect. These results suggest the presence of Sp1 proteins in the upper DNA-protein complex. The lower part of the complex may contain other members of the Sp family.

sequencing, and intron sizes were determined by PCR using oligos derived from flanking exons. All assigned exon/intron boundaries are in agreement with consensus 5'-GT and 3'-AG splicing sequences. The average length of the m-SmLIM/CRP2 exons, 145 bp, is consistent with the length of exons in general, i.e., 137 bp. Exon 1 contains the 5'-untranslated region. Exon 2 contains the entire 5' finger and the first cysteine of the 3' finger of the first LIM domain. Exon 3 contains the rest of 3' finger and the putative nuclear localization signal. Exon 4 encodes the first two cysteines of the 5' finger of the second LIM domain and exon 5 contains the rest of the 5' finger and most of the 3' finger except the last cysteine. Exon 6 contains the rest of the coding region and 3' untranslated region. At the 3' end of the m-SmLIM/CRP2 gene, exon 6 contains a consensus polyadenylation signal AATAAA motif. Poly(A) addition occurs 11 bp downstream from this motif.

TABLE 8 shows the m-SmLIM/CRP2 genomic sequence.

```
gtagggcgctgtctctaagtggtaactgcagcacacactcacacacacacagggtgctgtctgtct
ctaactggtaactgtaataaacacacacatacatacacaagcatacatagacacacacacacac
acacacacac...........ctgctcccagcaaacagccctttactggtggctagaagatatgac
agcaaagaggccagctttctagctgagccaaaccgtagcctgaggaggctgcttgtgcgctggttt
tcccagccacttgctgcatctagatcgagccaaaggaaacaagcctctcaatgtcctaactcagct
gtctcttccag (SEQ ID Nos:34,35)
```

-continued

```
EXON 5  CCCTGGCACAAAAACTGTTTCCGGTGTGCCAAGTGTGGGAAGAGTCTGGAGTCTACAACTCTGACT
         P  W  H  K  N  C  F  R  C  A  K  C  G  K  S  L  E  S  T  T  L  T
        GAGAAAGAAGGCGAAATCTACTGTAAAG (SEQ ID NO:36)
         E  K  E  G  E  I  Y  C  K  G (SEQ ID NO:37)

gtaaaaactcggttctgctgtctgttagtgtcaccagaaagggagacatcgtgcactgttaccttt
        tgaaaatgagaccgacatcttaggacagtgattacttcttccattcctactgtgtgttaagtcc
        acacggctggggatctggcccaatggtaaaagcttgcctatgtagcacattcacaaggaggccacg
        ctcagcacggcctcccaacctctgacttcctgctttaagccaagcatatgactacgtgagggtga
        cacacagaaggcagctggatttcagcctgcagcccatcacaatcctaacttggatgccgtgggaat
        tcctggactcgcttcaaacaaggatgctcatagcagagcccattttatatcttaaactgaccctcg
        cagagcctccagttcccttttaaattaatggccatttgttagtgacctctgattaactctcccttt
        cctttgtag (SEQ ID NO:38)

EXON 6  CGTGCTACGCAAAGAACTTTGGGCCCAAGGGATTTGGCTATGGTCAAGGGGCAGGGGCCCTTGTTC
          C  Y  A  K  N  F  G  P  K  G  F  G  Y  G  Q  G  A  G  A  L  V  H
        ATGCTCAGTAATGGTGTGAACCAGTAAGCACGACAGAGAATCTCCATTACCAAACTGCAGATGGCG
          A  Q  *  (SEQ ID NO:40)
        TTTATGGCGCTCACTACTGTGAAACAGCCAGCACTTGGCACTGGGCATCACCGAGCTGCCTGTGGG
        GGCTGGACCGACAGCGCTGCACTCTCCCGCCCACTCACTAGCGTCTAAGAGCATTCTTTTACATTT
        GAAATAAAATTTTGGCTTG (SEQ ID NO:39)

atttgggtaccacctcttaattaaccttcagaggagctgttgtgattttagatgatgagaagtt
        atctggttccttcctccagtgaaaaccagtctcctgattaaaaaaaaaaaaaagaccgtttcttta
        aaaagacaatcaattcctttatgcagtaggctaacatttgcactctgagagctgaaaacgacattt
        tactttgagattttcattcatatatatatatatatatatatatatatatatatatatatat
        atatatatatatatacaaaacactccgtgga (SEQ ID NO:17)
```

SmLIM/CRP2 is a highly conserved, two-LIM-domain nuclear protein of the LIM-only class. Other members of this class include RBTN2, MLP, and CRP. Like SmLIM/CRP2, RBTN2 and MLP are nuclear proteins with two LIM-domains, and they are highly conserved across species (Arber et al. 1994, Cell 79:221–231; Warren et al., 1994, Cell 78:45–57). CRP proteins also have two LIM-domains and show high cross-species conservation (Wang et al. 1992, J. Biol. Chem. 267:9176–9184; Weiskirchen et al., 1995, J. Biol. Chem. 270:28946–28954). Sequence comparisons of SmLIM/CRP2 and CRP suggest that the two gene families are related yet distinct (TABLES 2 and 3). In contrast with SmLIM/CRP2, which is a nuclear protein (FIGS. 2A and 2B), CRP has been localized to the cytoskeletal adhesion plaques (Crawford et al., 1994, J. Cell Biol. 124:117–127; Sadler et al., J. Cell Biol. 119:1573–1587). Moreover, h-SmLIM/CRP2 localizes to chromosome 3 (FIG. 3), whereas h-CRP localizes to chromosome 1 (Wang et al., 1992, Genomics 14:391–397). Finally, Northern analysis of r-CRP tissue distribution showed that the size of its mRNA and pattern of expression were distinct from those of r-SmLIM/CRP2. Taken together, these data indicate that SmLIM/CRP2 and CRP are distinct LIM proteins.

Cellular and Chromosomal Localization of SmLIM/CRP2

Figure 2A:
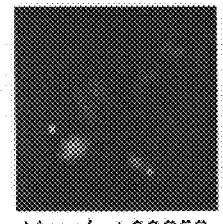
FIG. 2A is a photomicrograph of labeled cells. Cells immunostained with an anti-c-Myc antibody were counterstained with Hoechst 33258 to label the nuclei. Magnification, 600×.
Figure 2B:
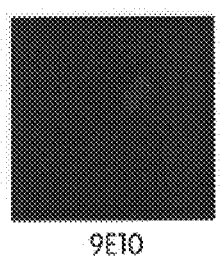
FIG. 2B is a photomicrograph of labeled cells showing the cellular localization of r-SmLIM/CRP2. COS cells were transiently transfected with the c-myc-r-SmLIM/CRP2 hybrid construct or vector alone. Protein expression was assayed 48 h after transfection with an anti-c-myc monoclonal antibody (9E10) followed by rhodamine-conjugated secondary antibody. Magnification, 600×.
Figure 3:
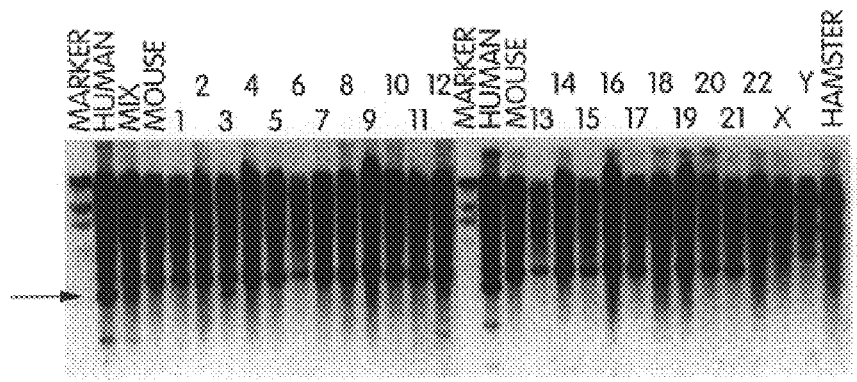
FIG. 3 is a photograph of a Southern blot assay showing chromosomal localization of human (h)-SmLIM/CRP2. Individual chromosomes are numbered 1–22, X, and Y. The three control DNA samples (human, mouse, and hamster) were provided by the manufacturer of the kit (BIOS Somatic Cell Hybrid Blot). Arrow indicates specific signal for h-SmLIM/CRP2 visible only in the human, mix, and chromosome 3 lanes.

The r-SmLIM/CRP2 deduced amino acid sequence contains the putative nuclear localization signal KKYGPK (SEQ ID NO:15), suggesting that SmLIM/CRP2 is a nuclear protein. To determine the cellular localization of SmLIM/CRP2, a plasmid expressing a fusion protein of the c-myc tag and r-SmLIM/CRP2 was made. This plasmid and the control vector alone were transfected into COS cells. The cells were immunostained with an anti-c-myc antibody. Detection of the immunofluorescent signal in the nuclei of COS cells transfected with the c-myc-r-SmLIM/CRP2 fusion plasmid but not the control vector alone indicated that the SmLIM/CRP2 protein localized to the nucleus (FIGS. 2A and 2B). The same experiment was performed with 10T1/2 fibroblasts. SmLIM/CRP2 localized to the nucleus in these cells as well. The chromosomal location of h-SmLIM/CRP2 was mapped with the BIOS Somatic Cell Hybrid Blot. h-SmLIM/CRP2 was found to localize to chromosome 3 (FIG. 3, arrow).

Tissue Distribution of r-SmLIM/CRP2 and h-SmLIM/CRP2

Figure 4A:
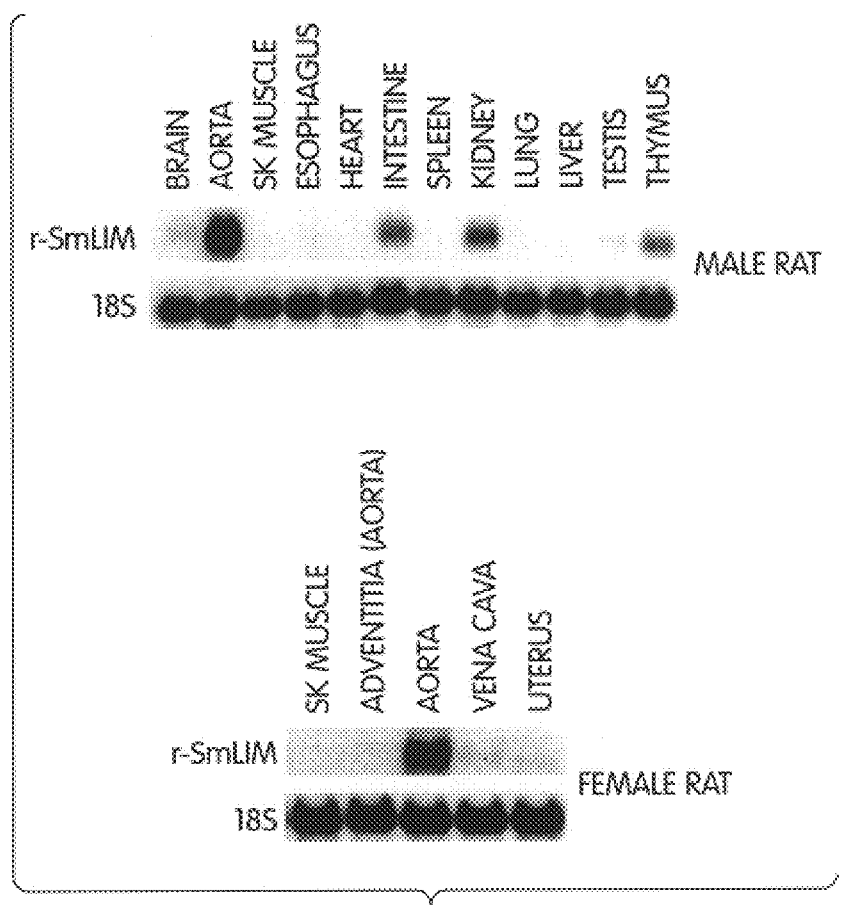
FIG. 4A is a photograph of a Northern blot assay showing r-SmLIM/CRP2 mRNA expression in male and female rat tissues. Northern analysis was performed with 10 µg of total RNA per lane. After electrophoresis, RNA was transferred to nitrocellulose filters and hybridized with a $^{32}$P-labeled r-SmLIM/CRP2 probe. A single r-SmLIM/CRP2 transcript is visible at 1.0 kb. Filters were hybridized with an 18S-specific probe to verify equivalent loading.
Figure 4B:
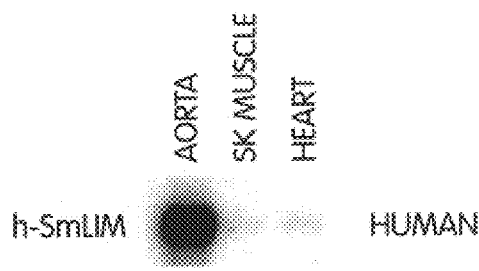
FIG. 4B is a photograph of a Northern blot assay showing h-SmLIM/CRP2 mRNA expression. Northern analysis was performed with 2 µg of poly A+ RNA (Clontech). A 2.1-kb transcript is shown.

Total RNA were isolated from 15 types of tissue from adult male and female rats and analyzed for SmLIM/CRP2 expression by Northern blot analysis (FIG. 4A). A single, intense, 1.0-kb band was detected in the aorta. A much weaker signal was detected in the kidney, thymus, and intestine. SmLIM/CRP2 expression was not detectable in heart and skeletal muscle and was barely detectable in brain, testis, esophagus, lung, liver, aortic adventitia, vena cava, and uterus. These data indicate that r-SmLIM/CRP2 is expressed in tissue containing smooth rather than striated muscle. Expression of SmLIM/CRP2 was found to be much greater in aortic tissue compared to intestinal or uterine tissue, indicating that SmLIM/CRP2 is expressed preferentially in vascular smooth muscle cells. Even among vascular RNAs, r-SmLIM/CRP2 expression was greater in arterial tissue (aorta) compared to venous tissue (vena cava). Consistent with the r-SmLIM/CRP2 expression pattern, h-SmLIM/CRP2 was expressed to a high degree in aorta but not in heart or skeletal muscle (FIG. 4B). The pattern of preferential expression in arterial but not venous smooth muscle cells suggests that smooth muscle cells may be fundamentally different in the two tissue types.

Although SmLIM/CRP2 is highly expressed in smooth uscle cells, it is not expressed in striated muscle cells (FIGS. 4A and 4B). This pattern is in contrast with that of MLP, which is expressed only in the heart and skeletal muscle. When a full-length MLP probe was hybridized to total RNA from aorta and cultured vascular smooth muscle cells, no message was detected. Thus, the expression of the two LIM proteins is distinct within the myogenic cell lineage.

Tissue Distribution of r-SmLIM/CRP2 (In Situ Hybridization)

Figure 5A:
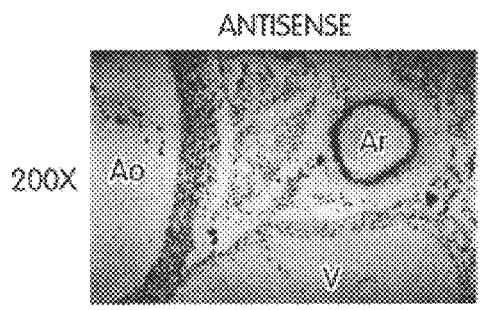
FIG. 5A is a photomicrograph of cells showing in situ hybridization of a r-SmLIM/CRP2 antisense probe to aorta (Ao), small artery (Ar), and vein (V) tissue sections at low magnification (200×).
Figure 5B:
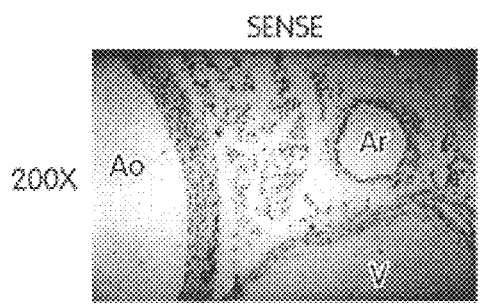
FIG. 5B is photomicrograph of cells showing in situ hybridization of a r-SmLIM/CRP2 sense probe to Ao, Ar, V tissue sections at low magnification (200×).
Figure 5C:
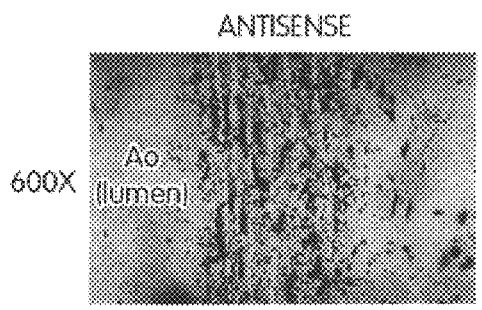
FIG. 5C is photomicrograph of cells showing in situ hybridization of a r-SmLIM/CRP2 antisense probe to Ao tissue at high magnification (600×).
Figure 5D:
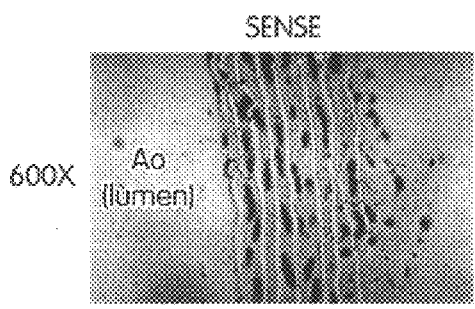
FIG. 5D is photomicrograph of cells showing in situ hybridization of a r-SmLIM/CRP2 sense probe to Ao tissue at high magnification (600×).

To localize r-SmLIM/CRP2 expression within the vessel wall, in situ hybridization was carried out. For each antisense experiment with the r-SmLIM/CRP2 riboprobe (FIGS. 5A and 5C), a corresponding sense (control) experiment (FIGS. 5B and 5D) was performed. FIG. 5A shows intense staining of r-SmLIM/CRP2 in both the aorta (Ao) and a small artery (Ar) nearby. Consistent with Northern analysis data, minimal expression of r-SmLIM/CRP2 was visible in the vena cava (V). A view of the aorta at higher magnification revealed that r-SmLIM/CRP2 expression was limited to smooth muscle cells in the medial layer (FIG. 5C). SmLIM/CRP2 signal expression was absent in skeletal muscle cells. These data indicate that r-SmLIM/CRP2 is expressed preferentially in arterial smooth muscle cells.

Figure 6A:
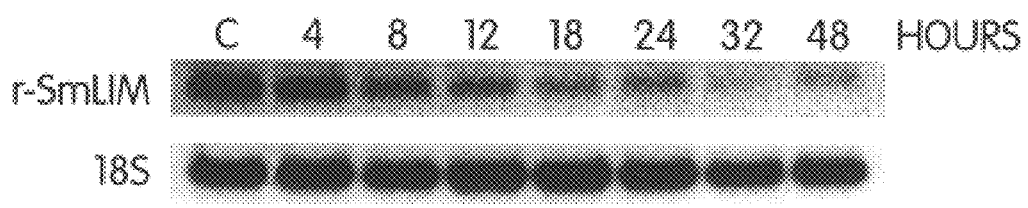
FIG. 6A is a photograph of a Northern blot assay showing a decrease in r-SmLIM/CRP2 mRNA expression in response to platelet derived growth factor-BB (PDGF-BB) treatment. Rat aortic smooth muscle cells were made quiescent by incubation in low-serum medium (DME plus 0.4% calf serum) for 48 h. Cells were then treated for the indicated times with PDGF-BB (20 ng/ml). Northern analysis was performed with 10 µg of total RNA per lane. After electrophoresis, RNA was transferred to nitrocellulose filters and hybridized with a $^2$P-labeled r-SmLIM/CRP2 probe. A single r-SmLIM/CRP2 transcript is visible at 1.0 kb. Filters were hybridized with an 18S-specific probe to verify equivalent sample loading.

Downregulation of r-SmLIM/CRP2 Expression in Vascular Smooth Muscle Cells by Growth Factors and Arterial Wall Injury PDGF-BB is unique among the smooth muscle cell mitogens in its ability to selectively suppress the expression of differentiation markers such as α-actin, smooth muscle myosin heavy chain, and α-tropomyosin in vitro. The effect of PDGF-BB on SmLIM/CRP2 expression was evaluated in cultured vascular smooth muscle cells. r-SmLIM/CRP2 mRNA levels decreased gradually in response to PDGF-BB stimulation (FIG. 6A). A decrease in r-SmLIM/CRP2 expression appeared as early as 4 h after treatment, and a maximal decrease of 80% was obtained at 32 h after treatment.

Figure 6B:
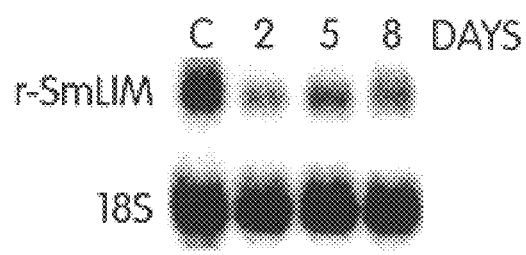
FIG. 6B is a photograph of a Northern blot assay showing a decrease in r-SmLIM/CRP2 mRNA expression after balloon injury in rat carotid arteries. Northern analysis was performed with 20 µg of total RNA per lane at 2, 5, and 8 days after injury. A single r-SmLIM/CRP2 transcript is visible at 1.0 kb. Filters were hybridized with an 18S-specific probe to verify equivalent sample loading.

In response to vessel wall injury, vascular smooth muscle cells undergo a phenotypic change from a differentiated, contractile state to a dedifferentiated, proliferative state. Balloon injury of the rat carotid artery was used to study this change in phenotype in vivo. Since smooth muscle cell proliferation after arterial injury reaches a maximum in the medial layer at 48 h and a maximum in the intimal layer at 96 h (and declines thereafter), r-SmLIM/CRP2 mRNA levels were evaluated at 2, 5, and 8 days after balloon injury of the carotid artery (FIG. 6B). SmLIM/CRP2 mRNA levels decreased by more than 60% after day 2 compared to the control, and remained at this level through day 8. These data indicate that r-SmLIM/CRP2 mRNA decreases in response to smooth muscle cell proliferation and dedifferentiation both in vitro and in vivo.

Developmental Regulation of r-SmLIM/CRP2 mRNA Expression

Figure 7A:
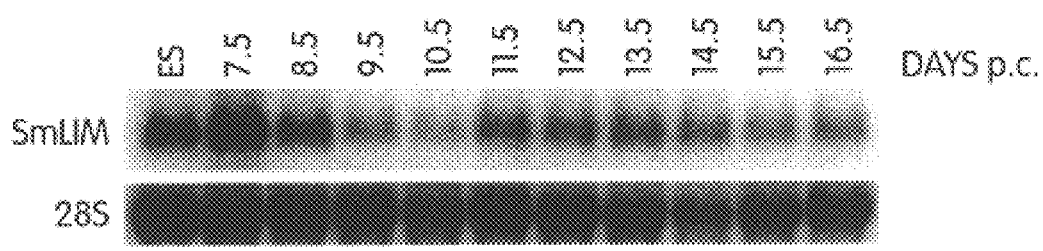
FIG. 7A is a photograph of a Northern blot assay showing expression of r-SmLIM/CRP2. Total RNA isolated from undifferentiated embryonic stem cells (ES) and mouse embryos from days 7.5–16.5 post coitum (p.c.). Northern analysis was performed with 10 µg of total RNA per lane. After electrophoresis, RNA was transferred to nitrocellulose filters and hybridized with a $^{32}$P-labeled r-SmLIM/CRP2 probe. A single r-SmLIM/CRP2 transcript is visible at 1.0 kb. Filters were hybridized with a 18S ribosomal probe to verify equivalent sample loading.
Figure 7B:
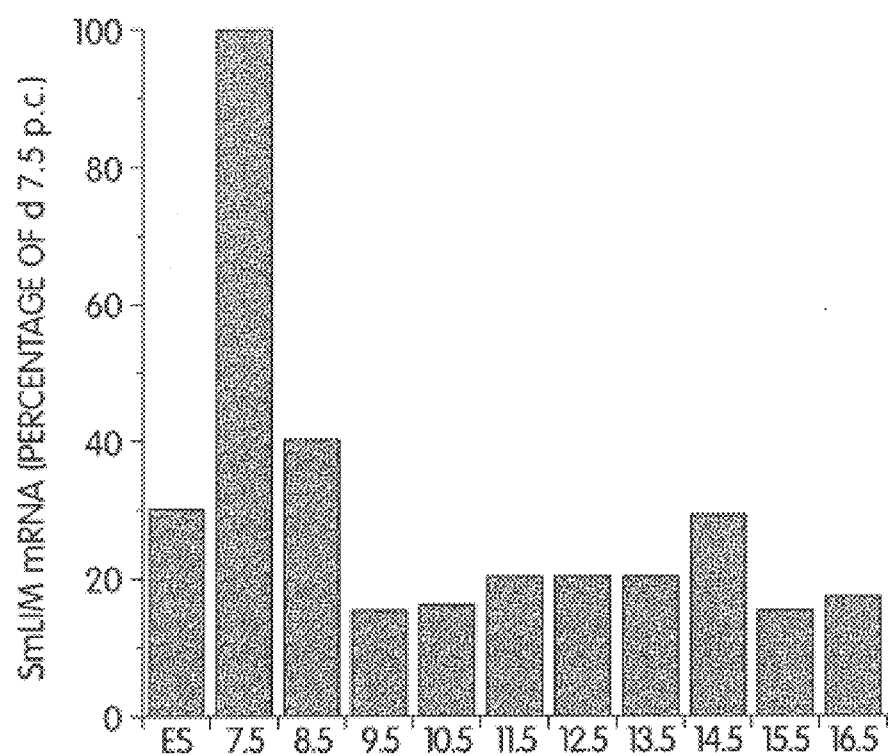
FIG. 7B is a bar graph showing the developmental regulation of SmLIM/CRP2 mRNA expression. The results of the Northern blot assay shown in FIG. 7A are graphically represented. The filters from the Northern blot assay were scanned to quantify the radioactivity.

SmLIM/CRP2 was found to be expressed preferentially in vascular tissue, and its levels are affected by the differentiation state of vascular smooth muscle cells. To determine whether SmLIM/CRP2 expression is regulated during development, total RNA was isolated from undifferentiated embryonic stem cells and whole mouse embryos at days 7.5–16.5 post coitum. SmLIM/CRP2 expression was found to be regulated developmentally (FIGS. 7A and 7B). Expression was highest during the late primitive streak stage (7.5 days p.c.), the point at which the embryonic and extraembryonic circulations begin to develop. SmLIM/CRP2 expression decreased rapidly at subsequent time points. The data normalized to the hybridization signal value at 7.5 days 30 p.c. (FIG. 7B). These data indicate that relative mRNA expression decreased by 40% at 8.5 days p.c. and by approximately 80% at 9.5–16.5 days p.c.

These data indicate that SmLIM/CRP2 expression is regulated developmentally. Expression is highest at day 7.5 p.c. in mouse embryos (FIGS. 7A and 7B) and plateaus by day 9.5 p.c. These early stages represent important points in the development of the mouse heart and vascular systems. At the late primitive streak stage (day 7.5 p.c.), discrete blood islands make their first appearance and amalgamate shortly thereafter to form the yolk sac vasculature. Within the embryo, the early formation of a vasculature is seen at 8.0 days p.c. and amalgamation of the embryonic and extraembryonic circulations at 8.5 days p.c. SmLIM/CRP2 expression was found to be highest in the adult aorta and correlates with the level of smooth muscle cell differentiation, and its embryonic expression is highest during periods critical for vascular development.

Deposit

A plasmid containing DNA encoding h-SmLIM/CRP2 (plasmid containing h-SmLIM/CRP2 cDNA) has been deposited with the American Type Culture Collection (ATCC) under the terms of the Budapest Treaty on the International Recognition of the Deposit of Microorganisms for the Purpose of Patent Procedure on Mar. 13, 1996, and bears the accession number 97470. Applicants' assignee, President and Fellows of Harvard College, acknowledges its duty to replace the deposit should the depository be unable to furnish a sample when requested due to the condition of the deposit before the end of the term of a patent issued hereon, and its responsibility to notify the ATCC of the issuance of such a patent, at which time the deposit will be made available to the public. Prior to that time, the deposit will be made available to the Commissioner of Patents under the terms of CFR §1.14 and 35 U.S.C. §112.

Generation of Transgenic SmLIM/CRP2 Null Mice

Figure 12A:
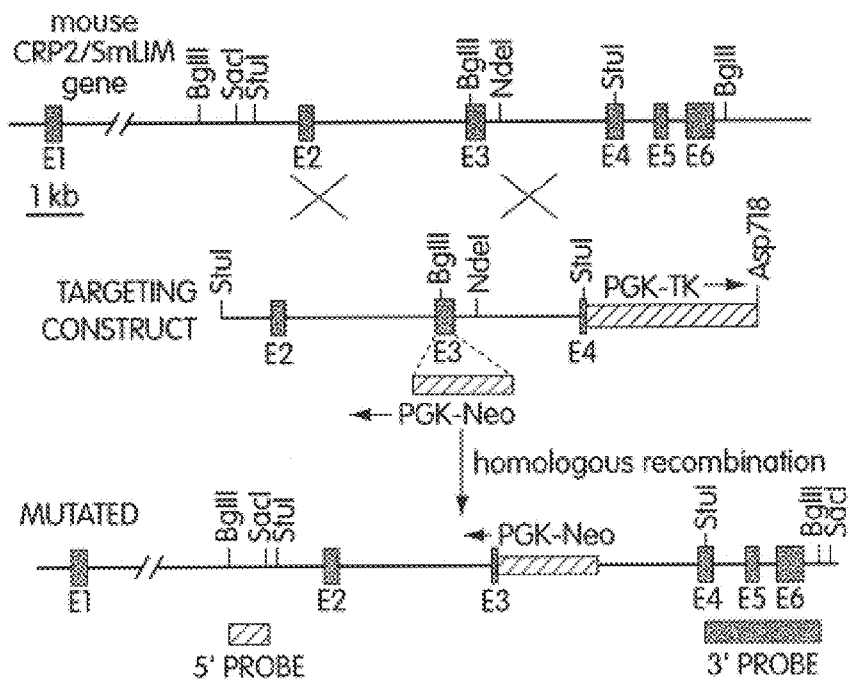
FIG. 12A is a diagram of mouse SmLIM/CRP2 genomic organization showing the knockout strategy for generating homozygous SmLIM-deficient mice.
Figure 12B:
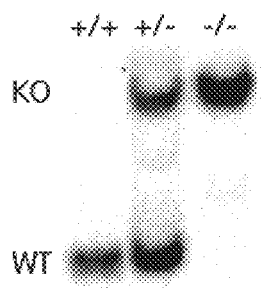
FIG. 12B is a autoradiograph of a Southern blot analysis used to identify SmLIM-deficient mice. Mouse tail DNA was digested with BglII and hybridized with a 5' external probe, which hybridized to a 5.3 kb endogenous fragment in wild-type (+/+ WT; normal) mice and heterozygous (+/−) mice, and an 11 kb mutated fragment in heterozygous and homozygous mutant (−/− KO; knockout) mice.
Figure 12C:
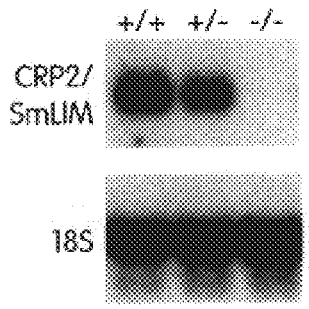
FIG. 12C is an autoradiograph of a Northern blot analysis of aorta RNA from wild-type (+/+), heterozygous (+/−), and homozygous mutant (−/−) mice.

To investigate the role of SmLIM/CRP2 in vivo, SmLIM knockout mice (SmLIM-deficient mice) were generated by homologous recombination. One copy of the SmLIM/CRP2 gene was disrupted. Mouse embryonic stem (ES) cells with the disruption were identified by both positive and negative selection procedures. A targeting construct was generated by replacing part of exon 3 and intron 3 with the neomycin resistance gene from PGK-neo. The genomic fragment was flanked at the 3' end with the herpes simplex virus thymidine kinase gene (PGK-tk) to allow negative selection with gancyclovir (FIG. 12A). D3 ES cells were transfected with a linearized SmLIM/CRP2 targeting construct by electroporation using known methods. Clones which were resistant to G418 (300 μg/ml) and gancyclovir (2 μM) were selected. Two hundred forty surviving clones were isolated after 7–8 days of selection. Southern blot analysis revealed six independent clones that had been properly targeted at the SmLIM locus. ES cells heterozygous for the targeted SmLIM/CRP2 allele were injected into blastocysts to generate chimeric mice. Breeding of chimeras with wild-type mice resulted in transmission of the mutation through the germ line and generation of SmLIM/CRP2 heterozygous mice, as demonstrated by Southern blot analysis with a 5' external probe or 3' external probe (FIG. 12B). Heterozygous mice, which were viable and fertile, were intercrossed to generate transgenic homozygous null mutant mice. These mice were born alive at the expected Mendelian ratio. Northern blot analysis with aortic RNA from wild-type, heterozygous, and homozygous mutant mice demonstrated that SmLIM/CRP2 message was absent in homozygous mutants (FIG. 12C).

SmLIM-deficient Mice are Resistant to Hypertension

The role of SmLIM in hypertension was studied using an art-recognized murine model of renovascular hypertension (Weisel et al., 1997, Hypertension 29:1025–30). A one-kidney, one clip (1K1C) model was used. The appropriate size of the clip lumen needed to induce high blood pressure was approximately 0.12 mm. For clipping, the renal artery of a kidney was individualized by blunt dissection and a clip placed closed to the aorta. Mice with a clipped vessel develop high blood pressure, e.g., approximately 20–35 mm Hg higher than corresponding sham-operated controls. The clipped mice also develop cardiovascular hypertrophy.

Figure 13:
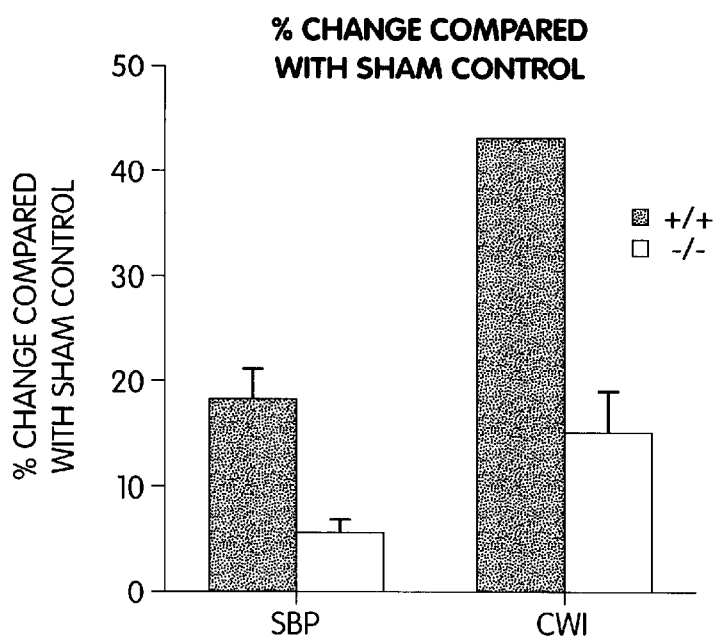
FIG. 13 is a bar graph showing % change in systolic blood pressure and cardiac weight index of wild-type and SmLIM knockout mice.
Figure 14:
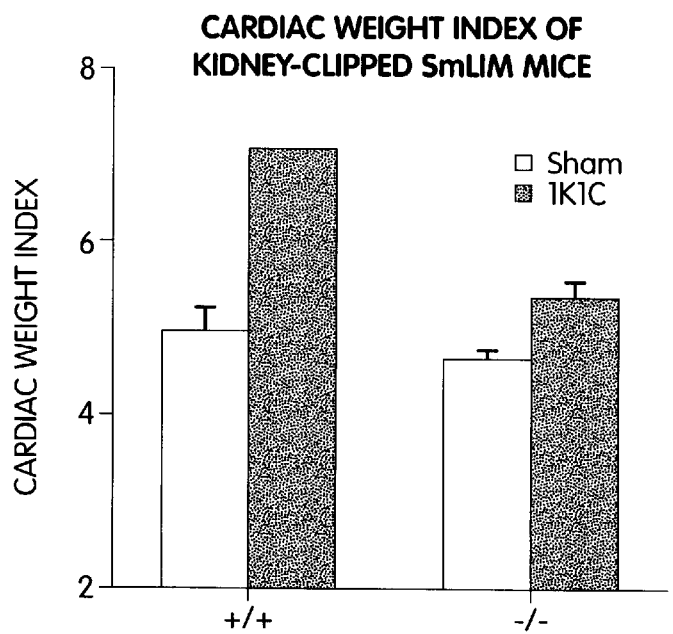
FIG. 14 is a bar graph showing cardiac weight index of kidney-clipped SmLIM knockout mice compared to sham control mice.
Figure 15:
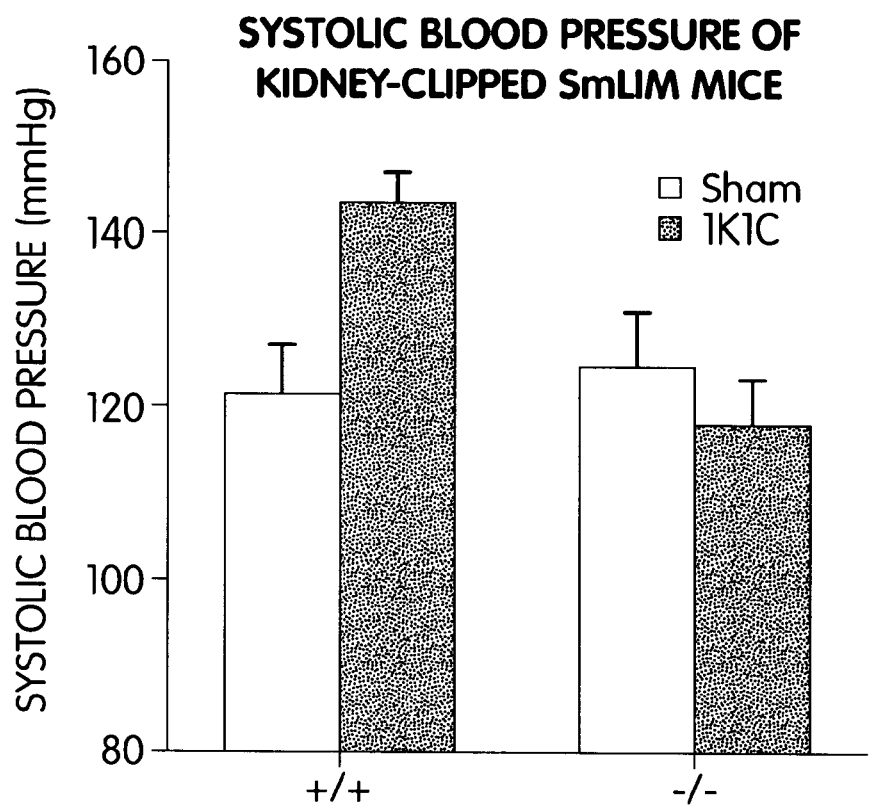
FIG. 15 is a bar graph showing systolic blood pressure of kidney-clipped SmLIM knockout mice compared to sham control mice.

SmLIM knockout mice were generated as described above. Both normal and SmLIM knockout mice were subjected to the 1K1C renovascular method of inducing hypertension. Systolic blood pressure and cardiac weight index (CWI; a measure of cardiac hypertrophy) was determined for knockout and normal mice (FIGS. 13–15). Consistent with the animal model, an increase in blood pressure (and CWI) was observed with the normal wildtype mice. In contrast, the SmLIM knockout mice did not develop hypertension despite an increase in CWI. These data indicate that hypertension is reduced by inhibiting the expression or function of SmLIM.

Identification of Compounds that Inhibit Expression or Function of SmLIM

Compounds that inhibit SmLIM expression or activity are identified by methods ranging from rational drug design to screening of random compounds. The latter method is preferable, as simple and rapid assays for testing such compounds are available. Small organic molecules are desirable candidate compounds for this analysis because such molecules are capable of passing through the plasma membrane to inhibit SmLIM production or activity within the cell.

Drugs which decrease SmLIM/CRP2 promoter activity are administered to decrease the level of expression of SmLIM/CRP2 in vascular tissue, e.g., arterial smooth muscle cells. Such drugs are identified by contacting a SmLIM/CRP2 regulatory sequence (e.g., SEQ ID NO:3 or 16) linked to a reporter gene with a candidate compound and measuring the level of expression of the reporter gene in the presence and absence of the compound. A decreased level of expression in the presence of the compound compared to that in its absence indicates that the compound inhibits the SmLIM/CRP2 promoter-directed transcription, e.g., transcription of endogenous SmLIM.

For example, the screening of compounds for the ability to inhibit SmLIM transcription are carried by identifying compounds that block the binding of trans-acting factors to SmLIM promoter sequences. The SmLIM promoter is linked to a reporter gene or a a 5' regulatory region of the SmLIM gene is linked to a functional promoter and a reporter gene, e.g., the gene encoding luciferase or alkaline phosphatase, and expression assays in the presence and absence of candidate inhibitory compounds are carried out using known methods. For luciferase constructs, the cells harboring the construct are harvested after exposure to the candidate compound and luciferase activity is measured; for alkaline phosphatase constructs, the culture medium of the cells is collected and the amount of alkaline phosphatase secreted by the cells into the medium is measured. A decrease in the amount of reporter activity indicates that the candidate compound inhibits SmLIM transcription.

SmLIM is involved in smooth muscle contraction. A ecrease in SmLIM expression or function leads to a decreased ability of smooth muscle cells to contract or develop tension. Inhibitory compounds (e.g., peptides, antibodies, or small organic molecules) which bind SmLIM are identified using standard binding assays. Compounds which bind to SmLIM are then tested for their ability to inhibit smooth muscle cell contraction (which contributes to hypertension). For example, a strip of smooth muscle cell tissue is contacted with catecholamine in the presence and absence of the candidate inhibitory compound, and smooth muscle cell contraction is measured. A decrease in smooth muscle cell contraction compared to the level of contraction in the absence of the candidate compound indicates that the compound decreases or prevents hypertension.

A variation of the above-described screening method can be used to screen for another class of candidate compounds which are capable of disrupting a SmLIM binding event such as dimerization. In this example, a complex comprising a SmLIM dimer is immobilized as described above and contacted with a candidate compound. The dissolution of the complex by the candidate compound correlates with the ability of the candidate compound to disrupt or inhibit SmLIM dimerization and thus SmLIM function.

Methods of Inhibiting Hypertension

SmLIM knockout mice are resistant to developing hypertension when subjected to conditions which induce hypertension in an art-recognized animal model of hypertension. The decrease in the incidence of hypertension in SmLIM deficient mice indicates that SmLIM contributes to the development of hypertension. Inhibition of hypertension is achieved by contacting vascular cells with a compound that inhibits SmLIM transcription and/or activity. For example, an inhibitory compound is a peptide, antibody, or small organic molecule that binds to SmLIM. Alternatively, the inhibitory compound is a nucleic acid, e.g., one that itself inhibits SmLIM transcription or translation or one that encodes an inhibitory peptide.

Nucleic acids complementary to all or part of the SmLIM coding sequence are administered to reduce translation of SmLIM mRNA. For example, the nucleic acid is at least 10 nucleotides in length which is complementary to at least a 10 nucleotide stretch of the SmLIM cDNA (Table 4; SEQ ID NO:4). For example, the antisense nucleic acid to be administered has the sequence of the complement of exon 2, 3, 4, or 5 of SmLIM-encoding DNA or a fragment of an SmLIM exon. An antisense nucleic acid may contain which is complementary to DNA encoding one or more LIM domains (indicated in bold face in Table 1) or DNA containing a nuclear localization sequence (underlined in Tables 1 and 5).

Antisense treatment is carried out by administering to a mammal such as a human patient, DNA containing a promoter, e.g., a vascular smooth muscle cell-specific promoter, operably linked to a DNA sequence (an antisense template), which is transcribed into an antisense RNA. For example, DNA containing SEQ ID NO:16 is operably linked to an SmLIM antisense template to target production of the antisense nucleic acid in vascular smooth muscle cells. DNA encoding a SmLIM inhibitory peptide, e.g., a peptide or intrabody that binds to a LIM domain, is operably linked to a vascular smooth muscle cell promoter such as SEQ ID NO:15, to direct production of the inhibitory peptide or intrabody in ascular smooth muscle cell target cells.

Alternatively, antisense oligonucleotides are introduced directly into vascular smooth muscle cell target cells. The antisense oligonucleotide may be a short nucleotide sequence (generally at least 10, preferably at least 14, more preferably at least 20 (e.g., at least 30), and up to 100 or more nucleotides) formulated to be complementary to a portion, e.g., the 5' non-coding region, the coding sequence, or all of SmLIM mRNA (e.g., one or more of exons 2, 3, 4, and 5). Standard methods relating to antisense technology have been described (see, e.g., Melani et al., 1991, Cancer Res. 51:2897–2901). Following transcription of a DNA sequence into an antisense RNA, the antisense RNA binds to its target nucleic acid molecule, such as an mRNA molecule, thereby inhibiting expression of the target nucleic acid molecule. For example, an antisense sequence complementary to a portion or all of SmLIM mRNA is used to inhibit the expression of SmLIM to reduce hypertension. Oligonucleotides complementary to various sequences of SmLIM mRNA are tested in vitro for their ability to decrease production of SmLIM, using assays described herein. Promising oligonucleotides are tested in viva in animals, e.g., mice subjected to the 1K1C hypertension model, to evaluate inhibition of hypertension.

Suitable vectors are known in the art. Preferred vectors are viral vectors, including those derived from replication-defective hepatitis viruses (e.g., HBV and HCV), retroviruses (see, e.g., WO 89/07136; Rosenberg et al., 1990, N. Eng. J. Med. 323(9):570–578), adenovirus (see, e.g., Morsey et al., 1993, J. Cell. Biochem., Supp. 17E,), adeno-associated virus (Kotin et al., 1990, Proc. Natl. Acad. Sci. USA 87:2211–2215,), replication defective herpes simplex viruses (HSV; Lu et al., 1992, Abstract, page 66, Abstracts of the Meeting on Gene Therapy, September 22–26, Cold Spring Harbor Laboratory, Cold Spring Harbor, N.Y.), and any modified versions of these vectors. The invention may utilize any other delivery system which accomplishes in vivo transfer of nucleic acids into eukaryotic cells. For example, the nucleic acids may be packaged into liposomes, receptor-mediated delivery systems, non-viral nucleic acid-based vectors, erythrocyte ghosts, or microspheres (e.g., microparticles; see, e.g., U.S. Pat. Nos. 4,789,734; 4,925,673; 3,625,214; Gregoriadis, 1979, Drug Carriers in Biology and Medicine, pp. 287–341 (Academic Press,). Alternatively, naked DNA may be administered.

Antisense oligonucleotides may consist of DNA, RNA, or any modifications or combinations thereof. As an example of the modifications that the oligonucleotides may contain, inter-nucleotide linkages other than phosphodiester bonds, such as phosphorothioate, methylphosphonate, methylphosphodiester, phosphorodithioate, phosphoramidate, phosphotriester, or phosphate ester linkages (Uhlman et al., 1990, Chem. Rev. 90(4):544–584; Anticancer Research, 1990, 10:1169) may be present in the oligonucleotides, resulting in their increased stability. Oligonucleotide stability is increased by incorporating 3'-deoxythymidine or 2'-substituted nucleotides (substituted with, e.g., alkyl groups) into the oligonucleotides during synthesis, by providing the oligonucleotides as phenylisourea derivatives, or by having other molecules, such as aminoacridine or poly-lysine, linked to the 3' ends of the oligonucleotides. Modifications of the RNA and/or DNA nucleotides may be present throughout the oligonucleotide, or in selected regions of the oligonucleotide, e.g., in the 5' and/or 3' ends. The antisense oligonucleotides are modified so as to increase their ability to penetrate the target tissue by, e.g., coupling the oligonucleotides to lipophilic compounds. ntisense oligonucleotides based on the SmLIM nucleotide equence are generated by any method known in the art, ncluding standard chemical synthesis, ligation of constituent oligonucleotides, and transcription of DNA complementary to the all or part of the SmLIM coding sequence. Antisense nucleic acids are administered alone or in admixture, or in chemical combination, with one or more materials, including other antisense oligonucleotides or recombinant vectors, materials that increase the biological stability of the oligonucleotides or the recombinant vectors, or materials that increase the ability of the therapeutic compositions to penetrate vascular smooth muscle cells selectively.

SmLIM activity is inhibited to treat patients suffering from hypertension or at risk of developing hypertension. For example, an antibody which binds to SmLIM is administered or intracellularly expressed to reduce binding to its intracellular ligand. For administration to human patients, antibodies, e.g., SmLIM-specific monoclonal antibodies, are humanized by methods known in the art. Antibodies with a desired binding specificity can be commercially humanized (Scotgene, Scotland; Oxford Molecular, Palo Alto, Calif.).

Anti-SmLIM antibodies are obtained using techniques well known in the art, e.g., those described herein. For example, an antibody was generated that binds to an epitope of mouse SmLIM having the amino acid sequence KPE-SAQPH (which corresponds to residue 91–98 of mouse SmLIM (SEQ ID NO:13). Antibodies which bind to one or both of the LIM domain are generated using methods known in the art, e.g., those described in U.S. Pat. No. 5,863,898. Such antibodies bind to a LIM domain and inhibit LIM-mediated dimerization. Following identification of a hybridoma producing a suitable monoclonal antibody, DNA encoding the antibody is cloned. DNA encoding a single chain SmLIM-specific antibody in which heavy and light chain variable domains is cloned into an expression vector using known methods (e.g., Marasco et al., 1993, Proc. Natl. Acad. Sci. USA 90:7889–7893 and Marasco et al., 1997, Gene Therapy 4:11–15). Such constructs are introduced into cells, e.g., using gene therapy techniques described herein, for intracellular production of the antibodies. Intracellular antibodies, i.e., intrabodies, are used to inhibit dimerization of SmLIM and/or binding of endogenous SmLIM to its intracelluar ligand, which in turn, decreases the activity of SmLIM and hypertension.

Methods of Treating Arteriosclerosis

The invention is based on the identification and characterization of a SmLIM/CRP2 polypeptide which is expressed preferentially in aortic smooth muscle cells. In vivo, SmLIM/CRP2 mRNA levels were found to decrease as vascular smooth muscle cells changed from a quiescent to a proliferative phenotype in response to vascular injury. Thus, administering SmLIM/CRP2 polypeptide or increasing expression of a SmLIM/CRP2-encoding DNA, e.g., by stimulating the SmLIM/CRP2 promoter or by introducing additional copies of SmLIM/CRP2-encoding DNA, in vascular smooth muscle cells which are injured or at risk of being injured can inhibit proliferation by promoting a quiescent, differentiated state.

An animal, e.g., a human patient, with arteriosclerosis or at risk of developing arteriosclerosis (and therefore in need of inhibition of arteriosclerosis or inhibition of vascular smooth muscle cell proliferation), may be identified using standard medical procedures, such as angiographic visualization of the lumen of a blood vessel, Doppler probes for measuring velocity and volume of blood flow, stress test, and ultrasound to detect arteriosclerotic plaques. Other patients in need of inhibition of arteriosclerosis or vascular smooth muscle cell proliferation are those with angina or stroke. Improvement of the patient's condition during and after therapy may be similarly monitored. Patients undergoing invasive vascular procedures, in particular balloon angioplasty, are also at risk for developing arteriosclerosis.

Angioplasty, used to treat arteriosclerosis, involves the insertion of catheters, e.g., balloon catheters, through an occluded region of a blood vessel in order to expand the lumenal opening. However, the aftermath of angioplasty may be problematic. Restenosis, or closing of the vessel, can occur as a consequence of injury, e.g., mechanical abrasion associated with the angioplasty treatment. This restenosis is believed to be caused by proliferation of smooth muscle cells stimulated by vascular injury. Other anatomical disruptions or mechanical disturbances of a blood vessel, e.g., attributable to laser angioplasty, coronary artery surgery, atherectomy and coronary artery stents, may also cause vascular injury and subsequent proliferation of smooth muscle cells. A SmLIM/CRP2 polypeptide, DNA encoding a SmLIM/CRP2 polypeptide, or compositions which stimulate expression from the SmLIM/CRP2 promoter may administered to increase the level of SmLIM/CRP2 polypeptide in the injured vascular tissue and thus inhibit the proliferation of smooth muscle cells.

SmLIM/CRP2 polypeptides may be administered to the patient intravenously in a pharmaceutically acceptable carrier such as physiological saline. Standard methods for intracellular delivery of peptides can be used, e.g. packaged in liposomes. Such methods are well known to those of ordinary skill in the art. It is expected that an intravenous dosage of approximately 1 to 100 μmoles of the polypeptide of the invention would be administered per kg of body weight per day. The compositions of the invention are useful for parenteral administration, such as intravenous, subcutaneous, intramuscular, and intraperitoneal routes.

Gene Therapy and Antisense Therapy

DNA (e.g., SmLIM/CRP2-encoding DNA, vascular cell-specific promoters, and vectors) of the invention may be introduced into target cells of the patient by standard vectors and/or gene delivery systems. Suitable gene delivery systems may include liposomes, receptor-mediated delivery systems, naked DNA, and viral vectors such as herpes viruses, retroviruses, and adenoviruses, among others. For example, the DNA of the invention under the control of a strong constitutive promoter may be administered locally to a blood vessel during balloon angioplasty using an adenovirus delivery system.

A vascular cell-specific promoter may be used to direct the expression of SmLIM/CRP2 or genes other than SmLIM/CRP2. Thus, vascular diseases may be treated by administering a vascular cell-specific promoter of the invention operatively linked to a sequence encoding a heterologous polypeptide, e.g., a SmLIM/CRP2 promoter linked to DNA encoding a growth inhibitor gene such as Rb, p21 or p18.

The invention can be used for gene therapy treatment of vascular diseases. The DNA of the invention can be used alone or as part of a vector to express heterologous genes, e.g., genes which encode proteins other than SmLIM/CRP2, in cells of the blood vessel wall, i.e., vascular smooth muscle cells, for gene therapy of vascular diseases such as arteriosclerosis. The DNA or vector containing a sequence encoding a polypeptide of interest is introduced into vascular smooth muscle cells which in turn produce the polypeptide of interest. For example, sequences encoding t-PA (Pennica et al., 1982, Nature 301:214), p21 cell cycle inhibitor (El-Deiry et al., 1993, Cell 75:817–823), or nitric oxide synthase (Bredt et al., 1990, Nature 347:768–770) may be operably linked to the vascular smooth muscle cell-specific promoter sequences of the invention and expressed in smooth muscle cells. For example, thrombolytic agents can be expressed under the control of the SmLIM/CRP2 promoter sequences for expression by vascular smooth muscle cells in blood vessels, e.g., vessels occluded by aberrant blood clots. Other heterologous proteins, e.g., proteins which inhibit smooth muscle cell proliferation, e.g., interferon-γ and atrial natriuretic polypeptide, may be specifically expressed in vascular smooth muscle cells to ensure the delivery of these therapeutic peptides to an arteriosclerotic lesion or an area at risk of developing an arteriosclerotic lesion, e.g., an injured blood vessel.

The SmLIM/CRP2 promoter sequences of the invention may also be used in gene therapy to promote angiogenesis to treat diseases such as peripheral vascular disease or coronary artery disease. For example, the promoter sequences can be operably linked to heterologous sequences encoding cellular growth factors which promote angiogenesis, e.g., VEGF, acidic fibroblast growth factor, or basic fibroblast growth factor.

According to the invention, the DNA of the invention is located sufficiently close to the coding sequence to be transcribed that it functions to direct expression of the polypeptide in vascular smooth muscle cell. For example, the promoter sequences are preferably located 5' to the transcription start site.

The DNA of the invention may also be used in methods of antisense therapy. Antisense therapy may be carried out by administering to an animal, e.g., a human patient, DNA containing the vascular smooth muscle cell-specific promoter sequences of the invention, e.g., SEQ ID NO:16, operably linked to a DNA sequence, i.e., an antisense template, which is transcribed into an antisense RNA. For example, the antisense template is transcribed into a SmLIM antisense RNA which binds to endogenous SmLIM transcripts and inhibits translation of the RNA into an SmLIM gene product. The antisense RNA may be a short (generally at least 10, preferably at least 14 nucleotides, and up to 100 or more nucleotides) nucleotide sequence formulated to be complementary to all or a portion of a specific mRNA sequence. The antisense template is preferably located downstream from the promoter sequences of the invention. A poly A tail is typically located at the end of the antisense sequence to signal the end of the sequence. Standard methods relating to antisense technology have been described (Melani et al., Cancer Res. 51:2897–2901, 1991). Following transcription of the DNA sequence into antisense RNA, the antisense RNA binds to its target mRNA molecules within a cell, thereby inhibiting translation of the mRNA and down-regulating expression of the protein encoded by the mRNA.

The expression of vascular smooth muscle cell proteins may be inhibited using antisense therapy. For example, the DNA of the invention can be operably linked to antisense templates which are transcribed into antisense RNA capable of inhibiting the expression of the smooth muscle cell proteins.

For gene therapy or antisense therapy, the claimed DNA may be introduced into target cells of an animal, e.g., a patient, using standard vectors and/or gene delivery systems. Suitable gene delivery systems may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy or antisense therapy may also be accomplished using a biolistic delivery system, such as that described by Williams et al., 1991, Proc. Natl. Acad. Sci. U.S.A. 88:2726–2729. Standard methods for transfecting cells with isolated DNA are well known to those skilled in the art of molecular biology. Gene therapy and antisense therapy to prevent or decrease the development of arteriosclerosis may be carried out by directly administering the claimed DNA to a patient or by transfecting vascular smooth cells with the claimed DNA ex vivo and infusing the transfected cells into the patient.

DNA or transfected cells may be administered in a pharmaceutically acceptable carrier. Pharmaceutically acceptable carriers are biologically compatible vehicles which are suitable for administration to an animal, e.g., physiological saline. A therapeutically effective amount is an amount of the DNA of the invention which is capable of producing a medically desirable result in a treated animal. As is well known in the medical arts, dosages for any one patient depends upon many factors, including the patient's size, body surface area, age, the particular compound to be administered, sex, time and route of administration, general health, and other drugs being administered concurrently. Dosages will vary, but a preferred dosage for intravenous administration of DNA is from approximately $10^6$ to $10^{22}$ copies of the DNA molecule. The compositions of the invention may be administered locally or systemically.

Administration will generally be parenterally, e.g., intravenously; DNA may also be administered directly to the target site, e.g., by biolistic delivery to an internal or external target site or by catheter to a site in an artery.

The preferred form of the composition to be administered depends on the intended mode of administration and therapeutic application. For example, SmLIM/CRP2 polypeptides or SmLIM/CRP2-encoding DNA may be administered in solution form through a catheter port or as a coating on the surface of a catheter, e.g., the balloon portion of a catheter used for balloon angioplasty.

Drugs which stimulate the SmLIM/CRP2 promoter may also be administered as described above to increase the level of expression of SmLIM/CRP2 in vascular tissue, e.g., arterial smooth muscle cells. Such drugs can be identified by contacting the SmLIM/CRP2 promoter linked to a reporter gene with a candidate compound and measuring the level of expression of the reporter gene in the presence and absence of the compound. An increased level of expression in the presence of the compound compared to that in its absence indicates that the compound stimulates the SmLIM/CRP2 promoter.

Methods of Diagnosis

The invention includes a method of detecting injury in a sample of vascular tissue. A depressed level of SmLIM/CRP2 polypeptide or transcript compared to the level in normal control vascular cells would predict a high degree of smooth muscle cell proliferation indicative of vascular tissue injury, e.g., restenosis. The diagnostic method of the invention is carried out by determining the level of SmLIM/CRP2 gene expression in a tissue, e.g, a vascular biopsy obtained at atherectomy. The level of gene expression may be measured using methods known in the art, e.g., in situ hybridization, Northern blot analysis, or Western blot analysis using SmLIM/CRP2-specific monoclonal or polyclonal antibodies. A decrease in the level of SmLIM/CRP2 expression in the test sample of tissue compared to the level per cell in uninjured control vascular tissue indicates the presence of a vascular injury in the test sample. It also indicates that the patient is a candidate for treatment with a therapeutic agent which increases the amount of SmLIM/CRP2 in the affected vascular smooth muscle cells. For example, tissue obtained at atherectomy could be tested for SmLIM/CRP2 expression, e.g., the level of SmLIM/CRP2 transcript or polypeptide. A depressed level of SmLIM/CRP2 transcript or polypeptide (compared to normal tissue) correlates with a high degree of smooth muscle cell proliferation indicating a high probability of restenosis. Such diagnostic procedures are useful to identify patients in need of therapeutic intervention to reduce or prevent restenosis.

Cells and Antibodies

Cells are transfected with the SmLIM/CRP2-encoding DNA using standard methods. Cells, e.g, vascular smooth muscle cells, expressing a SmLIM/CRP2 polypeptide, may be administered to an animal locally or systemically using intravenous, subcutaneous, intramuscular, and intraperitoneal delivery methods.

Alternatively, procaryotic or eucaryotic cells in culture can be transfected with the DNA of the invention operatively linked to expression control sequences appropriate for high-level expression in the cell. Such cells are useful for producing large amounts of the SmLIM/CRP2 polypeptide, which can be purified and used, e.g., as a therapeutic or for raising anti-SmLIM/CRP2 antibodies.

The anti-SmLIM/CRP2 antibodies useful in the present invention can be obtained by techniques well known in the art. Such antibodies can be polyclonal or monoclonal. Polyclonal antibodies can be obtained, for example, by the methods described in Ghose et al., Methods in Enzymology, Vol. 93, 326–327, 1983. For example, a SmLIM/CRP2 polypeptide, or an antigenic fragment thereof, can be used as the immunogen to stimulate the production of SmLIM/CRP2-reactive polyclonal antibodies in the antisera of animals such as rabbits, goats, sheep, rodents and the like.

The monoclonal antibodies useful in the present invention can be obtained by the process described by Milstein and Kohler in Nature, 256:495–97, 1975, or as modified by Gerhard, Monoclonal Antibodies, Plenum Press, 1980, pages 370–371. Hybridomas are screened to identify those producing antibodies that are highly specific for a SmLIM/CRP2 polypeptide. Preferably, the antibody will have an affinity of at least about $10^8$ liters/mole and more preferably, an affinity of at least about $10^9$ liters/mole. The use of such monoclonal antibodies provides a means of obtaining greater sensitivity in the assays of the present invention compared with the use of polyclonal antibodies.

Other embodiments are within the claims.

What is claimed is:

1. A method of decreasing hypertension in a mammal comprising administering to said mammal a compound that reduces expression of SmLIM by binding to a cis-acting regulatory sequence of a SmLIM gene, wherein said cis-acting regulatory sequence is SEQ ID NO: 3 or SEQ ID NO:16.

2. The method of claim 1, wherein said cis-acting regulatory sequence is SEQ ID NO:3.

3. The method of claim 1, wherein said cis-acting regulatory sequence is SEQ ID NO:16.

* * * * *

SEQUENCE LISTING

<160> NUMBER OF SEQ ID NOS: 46

<210> SEQ ID NO 1
<211> LENGTH: 193
<212> TYPE: PRT
<213> ORGANISM: Homo sapiens

<400> SEQUENCE: 1

Met Pro Val Trp Gly Gly Gly Asn Lys Cys Gly Ala Cys Gly Arg Thr
 1               5                  10                  15

Val Tyr His Ala Glu Glu Val Gln Cys Asp Gly Arg Ser Phe His Arg
            20                  25                  30

Cys Cys Phe Leu Cys Met Val Cys Arg Lys Asn Leu Asp Ser Thr Thr
        35                  40                  45

Val Ala Ile His Asp Glu Glu Ile Tyr Cys Lys Ser Cys Tyr Gly Lys
    50                  55                  60

Lys Tyr Gly Pro Lys Gly Tyr Gly Tyr Gln Gly Ala Gly Thr Leu
 65                  70                  75                  80

Asn Met Asp Arg Gly Glu Arg Leu Gly Ile Lys Pro Glu Ser Val Gln
             85                  90                  95

Pro His Arg Pro Thr Thr Asn Pro Asn Thr Ser Lys Phe Ala Gln Lys
            100                 105                 110

Tyr Gly Gly Ala Glu Lys Cys Ser Arg Cys Gly Asp Ser Val Tyr Ala
        115                 120                 125

Ala Glu Lys Ile Ile Gly Ala Gly Lys Pro Trp His Lys Asn Cys Phe
    130                 135                 140

Arg Cys Ala Lys Cys Gly Lys Ser Leu Glu Ser Thr Thr Leu Thr Glu
145                 150                 155                 160

Lys Glu Gly Glu Ile Tyr Cys Lys Gly Cys Tyr Ala Lys Asn Phe Gly
                165                 170                 175

Pro Lys Gly Phe Gly Tyr Gly Gln Gly Ala Gly Ala Lys Val His Ala
            180                 185                 190

Gln

<210> SEQ ID NO 2
<211> LENGTH: 741
<212> TYPE: DNA
<213> ORGANISM: Homo sapiens

<400> SEQUENCE: 2
atgcctgtct ggggaggtgg aaacaagtgt ggggcctgtg gaggaccgt gtaccacgca      60 gaagaggtgc agtgtgatgg caggagcttc accgctgct gctttctctg catggtttgc    120
aggaaaaatt tagatagcac aacagtggca attcacgatg aagagatcta ctgcaaatcc    180
tgctacggaa agaagtatgg gccaaaaggc tacggttatg ccagggcgc tggcacgctt    240 aacatggacc gtggcgagag gctgggcatc aaaccagaga gtgttcagcc tcacaggcct    300
acaacaaatc caaacacttc taaatttgct cagaaatatg gaggtgctga agtgttcc     360 agatgtgggg attctgtata tgctgccgag aagataattg gagctggaaa gccctggcac    420
aaaaactgtt tccgatgtgc aaagtgtggg aagagtcttg aatcaacaac tctgactgaa    480
aaagaaggtg aaatctattg taaaggatgc tatgcaaaga ctttgggcc aagggatt    540 ggctatggcc aaggagcagg ggctcttgtt catgcccagt aagatgtaaa ccctgaacta    600
aacatcacac actgagaatc tcttcataat ctaggcacag ataatcttta acccggaatt    660
ccgccgatac tgacgggctc caggagtcgt cgccaccaag ccgaattcca gcacactggc    720
ggccgttact agtggatccg a                                             741

<210> SEQ ID NO 3
<211> LENGTH: 427
<212> TYPE: DNA
<213> ORGANISM: Murinae gen. sp.

<400> SEQUENCE: 3
tgaggaatgc agctctttcg cgacaggaaa gctgcggatt ccagaagccg ggattctgac     60
cagagactat ctgcaccggg gagtcctgca ccccgagcta acatatggcg tttgtgcagt    120
aaaagggtgg cgggaatccc acggggcgac accggatctc gctggctccg ggccgatcct    180
gagtgctccg acgtcccgg accgcgggt aggagcagcc gagacgtggg agactcggac    240
gcgggaagcc gcaggaagag gcggattccg gtctttttgt ctcggggcca gagcacgaaa    300

```
cccgcatcgg atccccgagc tcacgccggg cggagaccat cgcacacccg agggggcatga    360 ccgatggctg agtcggaaca agccacgccc aacataagtc tttaaaagcg ggcacacgcg    420
tcccgcc                                                                427
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: PCR

<400> SEQUENCE: 4

```
gagtcttcac catgccgaac                                                  20
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: PCR

<400> SEQUENCE: 5

```
ctctcccacc ccaaaaatag                                                  20
```

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: c-MYC
      peptide tag

<400> SEQUENCE: 6

Glu Gln Lys Leu Ile Ser Glu Glu Asp
 1               5

<210> SEQ ID NO 7
<211> LENGTH: 880
<212> TYPE: DNA
<213> ORGANISM: Rattus sp.
<220> FEATURE:
<221> NAME/KEY: CDS
<222> LOCATION: (55)..(633)

<400> SEQUENCE: 7

```
acgagctaga cctccctagc tccgcccgcc gcgtgctccc gcctcccact cgga atg       57
                                                              Met
                                                                1 cct gtc tgg ggg ggt gga aat aag tgc ggg gcc tgc ggg aga acc gtg      105
Pro Val Trp Gly Gly Gly Asn Lys Cys Gly Ala Cys Gly Arg Thr Val
          5                  10                  15 tac cac gct gaa gag gtg cag tgt gat ggg cgg acg ttc cac cgc tgc      153
Tyr His Ala Glu Glu Val Gln Cys Asp Gly Arg Thr Phe His Arg Cys
             20                  25                  30 tgc ttt ctg tgc atg gtt tgc agg aaa aat tta gac agc aca aca gtg      201
Cys Phe Leu Cys Met Val Cys Arg Lys Asn Leu Asp Ser Thr Thr Val
         35                  40                  45 gca att cat gat gaa gag atc tac tgc aaa tca tgc tac gga aag aag      249
Ala Ile His Asp Glu Glu Ile Tyr Cys Lys Ser Cys Tyr Gly Lys Lys
     50                  55                  60                  65 tat gga cca aaa ggc tat ggt tat ggc cag ggc gct ggc acg ctc aac      297
Tyr Gly Pro Lys Gly Tyr Gly Tyr Gly Gln Gly Ala Gly Thr Leu Asn
                 70                  75                  80
```

```
atg gac cgt ggt gag agg ctg ggc atc aag cca gag agt gct caa cct    345
Met Asp Arg Gly Glu Arg Leu Gly Ile Lys Pro Glu Ser Ala Gln Pro
            85                  90                  95 cac agg cct aca aca aat cca aac act tct aaa ttt gcc cag aaa tat    393
His Arg Pro Thr Thr Asn Pro Asn Thr Ser Lys Phe Ala Gln Lys Tyr
        100                 105                 110 gga ggt gct gag aag tgc tcc aga tgt ggg gat tct gtg tat gct gct    441
Gly Gly Ala Glu Lys Cys Ser Arg Cys Gly Asp Ser Val Tyr Ala Ala
    115                 120                 125 gag aag atc att gga gct gga aag ccc tgg cac aaa aac tgt ttc cga    489
Glu Lys Ile Ile Gly Ala Gly Lys Pro Trp His Lys Asn Cys Phe Arg
130                 135                 140                 145 tgt gcc aag tgt ggg aag agt ctg gag tct aca act ctg act gag aag    537
Cys Ala Lys Cys Gly Lys Ser Leu Glu Ser Thr Thr Leu Thr Glu Lys
                150                 155                 160 gaa ggt gaa atc tac tgt aaa ggg tgc tac gca aag aac ttt ggg ccc    585
Glu Gly Glu Ile Tyr Cys Lys Gly Cys Tyr Ala Lys Asn Phe Gly Pro
            165                 170                 175 aag gga ttc ggc tat ggt caa gga gca ggg gcc ctt gtt cat gct cag    633
Lys Gly Phe Gly Tyr Gly Gln Gly Ala Gly Ala Leu Val His Ala Gln
        180                 185                 190 tagtggtgta aacccagtaa gcatggcaaa gaacctccat taatgtggat ggccttaccg    693
cactcaggct gtgcatcggc cagcactcag cactgtgtag cacacacgct atgtgcacaa    753
tcgggctgga caggaagcac tacactctcc tgcccatccg ctaacgttta agaacgttct    813
tttacatttg gaataaaatt ttggtttgat ttgaaaaaaa aaaaaaaaaa aaaaaaaaaa    873
aaaaaaa                                                                880

<210> SEQ ID NO 8
<211> LENGTH: 193
<212> TYPE: PRT
<213> ORGANISM: Rattus sp.

<400> SEQUENCE: 8

Met Pro Val Trp Gly Gly Asn Lys Cys Gly Ala Cys Gly Arg Thr
  1               5                  10                  15

Val Tyr His Ala Glu Glu Val Gln Cys Asp Gly Arg Thr Phe His Arg
                20                  25                  30

Cys Cys Phe Leu Cys Met Val Cys Arg Lys Asn Leu Asp Ser Thr Thr
            35                  40                  45

Val Ala Ile His Asp Glu Ile Tyr Cys Lys Ser Cys Tyr Gly Lys
        50                  55                  60

Lys Tyr Gly Pro Lys Gly Tyr Gly Tyr Gln Gly Ala Gly Thr Leu
 65                 70                  75                  80

Asn Met Asp Arg Gly Glu Arg Leu Gly Ile Lys Pro Glu Ser Ala Gln
                85                  90                  95

Pro His Arg Pro Thr Thr Asn Pro Asn Thr Ser Lys Phe Ala Gln Lys
            100                 105                 110

Tyr Gly Gly Ala Glu Lys Cys Ser Arg Cys Gly Asp Ser Val Tyr Ala
        115                 120                 125

Ala Glu Lys Ile Ile Gly Ala Gly Lys Pro Trp His Lys Asn Cys Phe
    130                 135                 140

Arg Cys Ala Lys Cys Gly Lys Ser Leu Glu Ser Thr Thr Leu Thr Glu
145                 150                 155                 160

Lys Glu Gly Glu Ile Tyr Cys Lys Gly Cys Tyr Ala Lys Asn Phe Gly
                165                 170                 175
```

```
Pro Lys Gly Phe Gly Tyr Gly Gln Gly Ala Gly Ala Leu Val His Ala
            180                 185                 190
Gln

<210> SEQ ID NO 9
<211> LENGTH: 193
<212> TYPE: PRT
<213> ORGANISM: Rattus sp.

<400> SEQUENCE: 9

Met Pro Asn Trp Gly Gly Gly Lys Lys Cys Gly Val Cys Gln Lys Thr
  1               5                  10                  15

Val Tyr Phe Ala Glu Glu Val Gln Cys Glu Gly Asn Ser Phe His Lys
             20                  25                  30

Ser Cys Phe Leu Cys Met Val Cys Lys Lys Asn Leu Asp Ser Thr Thr
         35                  40                  45

Val Ala Val His Gly Glu Glu Ile Tyr Cys Lys Ser Cys Tyr Gly Lys
     50                  55                  60

Lys Tyr Gly Pro Lys Gly Tyr Gly Tyr Gly Gln Gly Ala Gly Thr Leu
 65                  70                  75                  80

Ser Met Asp Lys Gly Glu Ser Leu Gly Ile Lys His Glu Glu Ala Pro
                 85                  90                  95

Gly His Arg Pro Thr Thr Asn Pro Asn Ala Ser Lys Phe Ala Gln Lys
            100                 105                 110

Ile Gly Gly Ser Glu Arg Cys Pro Arg Cys Ser Gln Ala Val Tyr Ala
            115                 120                 125

Ala Glu Lys Val Ile Gly Ala Gly Lys Ser Trp His Lys Ser Cys Phe
        130                 135                 140

Arg Cys Ala Lys Cys Gly Lys Gly Leu Glu Ser Thr Thr Leu Ala Asp
145                 150                 155                 160

Lys Asp Gly Glu Ile Tyr Cys Lys Gly Cys Tyr Ala Lys Asn Phe Gly
                165                 170                 175

Pro Lys Gly Phe Gly Phe Gly Gln Gly Ala Gly Ala Leu Val His Ser
            180                 185                 190
Glu

<210> SEQ ID NO 10
<211> LENGTH: 193
<212> TYPE: PRT
<213> ORGANISM: Rattus sp.

<400> SEQUENCE: 10

Met Pro Asn Trp Gly Gly Gly Lys Lys Cys Gly Val Cys Gln Lys Thr
  1               5                  10                  15

Val Tyr Phe Ala Glu Glu Val Gln Cys Glu Gly Asn Ser Phe His Lys
             20                  25                  30

Ser Cys Phe Leu Cys Met Val Cys Lys Lys Asn Leu Asp Ser Thr Thr
         35                  40                  45

Val Ala Val His Gly Glu Glu Ile Tyr Cys Lys Ser Cys Tyr Gly Lys
     50                  55                  60

Lys Tyr Gly Pro Lys Gly Tyr Gly Tyr Gly Gln Gly Ala Gly Thr Leu
 65                  70                  75                  80

Ser Thr Asp Lys Gly Glu Ser Leu Gly Ile Lys Gly Glu Glu Ala Pro
                 85                  90                  95

Gly His Arg Pro Thr Thr Asn Pro Asn Ala Ser Lys Phe Ala Gln Lys
            100                 105                 110
```

```
Ile Gly Gly Ser Glu Arg Cys Pro Arg Cys Ser Gln Ala Val Tyr Ala
            115                 120                 125

Ala Glu Lys Val Ile Gly Ala Gly Lys Ser Gln His Lys Ala Cys Phe
        130                 135                 140

Arg Cys Ala Lys Cys Gly Lys Gly Leu Glu Ser Thr Thr Leu Ala Asp
145                 150                 155                 160

Lys Asp Gly Glu Ile Tyr Cys Lys Gly Cys Tyr Ala Lys Asn Phe Gly
                165                 170                 175

Pro Lys Gly Phe Gly Phe Gly Gln Gly Ala Gly Leu Val His Ser
            180                 185                 190

Glu

<210> SEQ ID NO 11
<211> LENGTH: 194
<212> TYPE: PRT
<213> ORGANISM: Homo sapiens

<400> SEQUENCE: 11

Met Pro Asn Trp Gly Gly Gly Ala Lys Cys Gly Ala Cys Asp Lys Thr
1               5                   10                  15

Val Tyr Gly Ala Glu Glu Ile Gln Cys Asn Gly Arg Ser Phe His Lys
            20                  25                  30

Thr Cys Phe His Cys Met Ala Cys Arg Lys Ala Leu Asp Ser Thr Thr
        35                  40                  45

Val Ala Ala His Glu Ser Glu Ile Tyr Cys Lys Val Cys Tyr Gly Arg
    50                  55                  60

Lys Tyr Gly Pro Lys Gly Ile Gly Phe Gly Gln Gly Ala Gly Cys Leu
65                  70                  75                  80

Ser Thr Asp Thr Gly Glu His Leu Gly Leu Gln Phe Gln Gln Ser Pro
                85                  90                  95

Lys Pro Ala Arg Ala Ala Thr Thr Ser Asn Pro Ser Lys Phe Ser Ala
            100                 105                 110

Lys Phe Gly Glu Ser Glu Lys Cys Pro Arg Cys Gly Lys Ser Val Tyr
        115                 120                 125

Ala Ala Glu Lys Val Met Gly Gly Gly Lys Pro Trp His Lys Thr Cys
    130                 135                 140

Phe Pro Cys Ala Ile Cys Gly Lys Ser Leu Glu Ser Thr Asn Val Thr
145                 150                 155                 160

Asp Lys Asp Gly Glu Leu Tyr Cys Lys Val Cys Tyr Ala Lys Asn Phe
                165                 170                 175

Gly Pro Thr Gly Ile Gly Phe Gly Gly Leu Thr His Gln Val Glu Lys
            180                 185                 190

Lys Glu

<210> SEQ ID NO 12
<211> LENGTH: 194
<212> TYPE: PRT
<213> ORGANISM: Rattus sp.
<220> FEATURE:
<221> NAME/KEY: VARIANT
<222> LOCATION: (1)..(194)
<223> OTHER INFORMATION: where Xaa can be an amino acid as defined in
      the specification

<400> SEQUENCE: 12

Met Pro Xaa Trp Gly Gly Gly Xaa Lys Cys Gly Xaa Cys Xaa Xaa Thr
1               5                   10                  15
```

-continued

```
Val Tyr Xaa Ala Glu Glu Val Gln Cys Xaa Gly Xaa Xaa Phe His Xaa
            20                  25                  30

Xaa Cys Phe Xaa Cys Met Xaa Cys Xaa Lys Xaa Leu Asp Ser Thr Thr
        35                  40                  45

Val Ala Xaa His Xaa Xaa Glu Ile Tyr Cys Lys Xaa Cys Tyr Gly Xaa
    50                  55                  60

Lys Tyr Gly Pro Lys Gly Xaa Gly Tyr Gly Trp Gly Ala Gly Xaa Leu
65                  70                  75                  80

Xaa Xaa Asp Xaa Gly Glu Xaa Leu Gly Xaa Xaa Xaa Xaa Xaa Xaa Xaa
                85                  90                  95

Xaa Xaa Xaa Arg Xaa Xaa Thr Xaa Xaa Asn Xaa Ser Lys Phe Xaa Xaa
            100                 105                 110

Lys Xaa Gly Xaa Xaa Glu Xaa Cys Xaa Arg Cys Xaa Xaa Xaa Val Tyr
        115                 120                 125

Ala Ala Glu Lys Xaa Xaa Gly Xaa Gly Lys Xaa Trp His Lys Xaa Cys
    130                 135                 140

Phe Xaa Cys Ala Xaa Cys Gly Lys Xaa Leu Glu Ser Thr Xaa Xaa Xaa
145                 150                 155                 160

Xaa Lys Xaa Gly Glu Xaa Tyr Cys Lys Xaa Cys Tyr Ala Lys Asn Phe
                165                 170                 175

Gly Pro Xaa Gly Xaa Gly Xaa Gly Xaa Xaa Xaa Xaa Xaa Xaa Xaa Xaa
            180                 185                 190

Xaa Xaa

<210> SEQ ID NO 13
<211> LENGTH: 193
<212> TYPE: PRT
<213> ORGANISM: Artificial Sequence
<220> FEATURE:
<223> OTHER INFORMATION: Description of Artificial Sequence: consensus
<400> SEQUENCE: 13

Met Pro Val Trp Gly Gly Gly Asn Lys Cys Gly Ala Cys Gly Arg Thr
  1               5                  10                  15

Val Tyr His Ala Glu Glu Val Gln Cys Asp Gly Arg Thr Phe His Arg
            20                  25                  30

Cys Cys Phe Leu Cys Met Val Cys Arg Lys Asn Leu Asp Ser Thr Thr
        35                  40                  45

Val Ala Ile His Asp Glu Glu Ile Tyr Cys Lys Ser Cys Tyr Gly Lys
    50                  55                  60

Lys Tyr Gly Pro Lys Gly Tyr Gly Tyr Gly Gln Gly Ala Gly Thr Leu
65                  70                  75                  80

Asn Met Asp Arg Gly Glu Arg Leu Gly Ile Lys Pro Glu Ser Ala Gln
                85                  90                  95

Pro His Arg Pro Thr Thr Asn Pro Asn Thr Ser Lys Phe Ala Gln Lys
            100                 105                 110

Tyr Gly Gly Ala Glu Lys Cys Ser Arg Cys Gly Asp Ser Val Tyr Ala
        115                 120                 125

Ala Glu Lys Ile Ile Gly Ala Gly Lys Pro Trp His Lys Asn Cys Phe
    130                 135                 140

Arg Cys Ala Lys Cys Gly Lys Ser Leu Glu Ser Thr Thr Leu Thr Glu
145                 150                 155                 160

Lys Glu Gly Glu Ile Tyr Cys Lys Gly Cys Tyr Ala Lys Asn Phe Gly
                165                 170                 175

Pro Lys Gly Phe Gly Tyr Gly Gln Gly Ala Gly Ala Leu Val His Ala
        180                 185                 190
Gln

<210> SEQ ID NO 14
<211> LENGTH: 840
<212> TYPE: DNA
<213> ORGANISM: Murinae gen. sp.

<400> SEQUENCE: 14

| | | | | | |
|---|---|---|---|---|---|
| agtctccgga | tccgcccgcg | gctttcctcg | gtcagacctc | gttagctccg | cccgccgcgt | 60 |
| gctccctcct | cccactcgga | atgcctgtct | ggggcggtgg | aaataagtgc | ggggcctgcg | 120 |
| ggagaaccgt | gtaccacgcg | gaagaggtgc | agtgcgatgg | gcggacgttc | catcgctgct | 180 |
| gcttcctgtg | catggtttgc | aggaaaaatt | tagacagcac | aacagtggcg | attcatgatg | 240 |
| aagagatcta | ctgcaaatcc | tgctacggaa | agaagtatgg | accaaaaggc | tatggttatg | 300 |
| gccagggcgc | tggcacgctc | aacatggacc | gcggtgagag | actgggcatc | aagccagaga | 360 |
| gtgctcaacc | tcacaggcct | acgacaaatc | caaacacttc | taaatttgcc | cagaaatatg | 420 |
| gaggagctga | gaagtgttcc | aggtgtgggg | attccgtgta | tgctgcggag | aagatcattg | 480 |
| gagctgggaa | gccctggcac | aaaaactgtt | tccggtgtgc | caagtgtggg | aagagtctgg | 540 |
| agtctacaac | tctgactgag | aaagaaggcg | aaatctactg | taaagggtgc | tacgcaaaga | 600 |
| actttgggcc | caagggattt | ggctatggtc | aaggggcagg | ggcccttgtt | catgctcagt | 660 |
| aatggtgtga | accagtaagc | acgacagaga | atctccatta | ccaaactgca | gatggcgttt | 720 |
| atggcgctca | ctactgtgaa | acagccagca | cttggcactg | gcatcaccg | agctgcctgt | 780 |
| gggggctgga | ccgacagcgc | tgcactctcc | cgcccactca | ctagcgtcta | agagcattct | 840 |

<210> SEQ ID NO 15
<211> LENGTH: 6
<212> TYPE: PRT
<213> ORGANISM: Murinae gen. sp.

<400> SEQUENCE: 15

Lys Lys Tyr Gly Pro Lys
 1               5

<210> SEQ ID NO 16
<211> LENGTH: 522
<212> TYPE: DNA
<213> ORGANISM: Artificial Sequence
<220> FEATURE:
<223> OTHER INFORMATION: Description of Artificial Sequence: artif

<400> SEQUENCE: 16

| | | | | | |
|---|---|---|---|---|---|
| tgaggaatgc | agctctttcg | cgacaggaaa | gctgcggatt | ccagaagccg | ggattctgac | 60 |
| cagagactat | ctgcaccggg | gagtcctgca | ccccgagcta | acatatggcg | tttgtgcagt | 120 |
| aaaagggtgg | cgggaatccc | acggggcgac | accggatctc | gctggctccg | ggccgatcct | 180 |
| gagtgctccg | gacgtcccgg | gaccgcgggt | aggagcagcc | gagacgtggg | agactcggac | 240 |
| gcgggaagcc | gcaggaagag | gcggattccg | gtcttttttgt | ctcggggcca | gagcacgaaa | 300 |
| cccgcatcgg | atccccgagc | tcacgccggg | cggagaccat | cgcacacccg | aggggcatga | 360 |
| ccgatggctg | agtcggaaca | agccacgccc | aacataagtc | tttaaaagcg | ggcacacgcg | 420 |
| tcccgccagt | ctccggatcc | gcccgccggc | tttcctcggt | cagacctcgt | tagctccgcc | 480 |
| cgccgcgtgc | tccctcctcc | cactcgggtg | agtcctaggc | tc | | 522 |

<210> SEQ ID NO 17
<211> LENGTH: 297
<212> TYPE: DNA
<213> ORGANISM: Murinae gen. sp.

<400> SEQUENCE: 17
atttgggtac cacctcttaa ttaacctttc agaggagctg ttgtgatttt tagatgatga    60
gaagttatct ggttccttcc tccagtgaaa accagtctcc tgattaaaaa aaaaaaaaag   120
accgtttctt taaaaagaca atcaattcct ttatgcagta ggctaacatt tgcactctga   180
gagctgaaaa cgacatttta cttttgagat tttcattcat atatatatat atatatacat   240
atatatatat atatatatat atatatatat atatatatat acaaaacact ccgtgga      297

<210> SEQ ID NO 18
<211> LENGTH: 52
<212> TYPE: PRT
<213> ORGANISM: Murinae gen. sp.
<220> FEATURE:
<221> NAME/KEY: VARIANT
<222> LOCATION: (1)..(52)
<223> OTHER INFORMATION: where Xaa can be any amino acid as defined in
      the specification

<400> SEQUENCE: 18

Cys Xaa Xaa Cys Xaa Xaa Xaa Xaa Xaa Xaa Xaa Xaa Xaa Xaa Xaa
  1               5                  10                  15

Xaa Xaa Xaa Xaa Xaa His Xaa Xaa Cys Xaa Xaa Cys Xaa Xaa Cys Xaa
             20                  25                  30

Xaa Xaa Xaa Xaa Xaa Xaa Xaa Xaa Xaa Xaa Xaa Xaa Xaa Xaa Xaa
         35                  40                  45

Cys Xaa Xaa Xaa
     50

<210> SEQ ID NO 19
<211> LENGTH: 79
<212> TYPE: DNA
<213> ORGANISM: Artificial Sequence
<220> FEATURE:
<223> OTHER INFORMATION: Description of Artificial Sequence: as in
      specification

<400> SEQUENCE: 19
agtctccgga tccgcccgcg gctttcctcg gtcagacctc gttagctccg cccgccgcgt    60
gctccctcct cccactcgg                                                 79

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: as in
      specification

<400> SEQUENCE: 20
gtgagtccta ggctc                                                     15

<210> SEQ ID NO 21
<211> LENGTH: 215
<212> TYPE: DNA
<213> ORGANISM: Artificial Sequence
<220> FEATURE:
<223> OTHER INFORMATION: Description of Artificial Sequence: as in specification

<400> SEQUENCE: 21

| gagctctgtg agtaagagcg atgtttcctc cacgatatgc tagataaaaa tctgggggtg | 60 |
| gggggtaacc agaagaggga caaagcacct tgtactaatt gtttaaatat ttaataaagg | 120 |
| tctcatcagg aaacctaata gaggtctgca ccatttaatg gttgtatggg aatcacgcct | 180 |
| ttaaggcaaa gatgagcttt ctctgctaca gacta | 215 |

<210> SEQ ID NO 22
<211> LENGTH: 90
<212> TYPE: DNA
<213> ORGANISM: Artificial Sequence
<220> FEATURE:
<223> OTHER INFORMATION: Description of Artificial Sequence: as in
      specification

<400> SEQUENCE: 22

| aagcatctgc tagtacgcac tgtctcgtgg ctgaagcagc cggagggaac tcgtaaaaca | 60 |
| acgcatccta atgcatcctt tgttccgcag | 90 |

<210> SEQ ID NO 23
<211> LENGTH: 113
<212> TYPE: DNA
<213> ORGANISM: Artificial Sequence
<220> FEATURE:
<223> OTHER INFORMATION: Description of Artificial Sequence: as in
      specification

<400> SEQUENCE: 23

| catgcctgtc tggggcggtg gaaataagtg cggggcctgc gggagaaccg tgtaccacgc | 60 |
| ggaagaggtg cagtgcgatg ggcggacgtt ccatcgctgc tgcttcctgt gca | 113 |

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: as in
      specification

<400> SEQUENCE: 24

Met Pro Val Trp Gly Gly Gly Asn Lys Cys Gly Ala Cys Gly Arg Thr
 1               5                  10                  15

Val Tyr His Ala Glu Glu Val Gln Cys Asp Gly Arg Thr Phe His Arg
            20                  25                  30

Cys Cys Phe Leu Cys Met
        35

<210> SEQ ID NO 25
<211> LENGTH: 256
<212> TYPE: DNA
<213> ORGANISM: Artificial Sequence
<220> FEATURE:
<223> OTHER INFORMATION: Description of Artificial Sequence: as in
      specification

<400> SEQUENCE: 25

| gtgagtatgg tcccctcccc cttcagttca cctctggaag aaaataacaa atgctagcta | 60 |
| agagaaatgg tttagagtga cggggttttt tgtttgtttg ttttttgttt taaccgctga | 120 |
| gtcatctctc tagcccaatg cggtgtttta tgtcattgat cttaagacgc tgaggactga | 180 |

```
gccagaggga agaccaccta gccctcagtt ctggccagtt ggcttagcct ttgtcacctc    240
tgtctgtgtc ctcggg                                                    256
```

<210> SEQ ID NO 26
<211> LENGTH: 129
<212> TYPE: DNA
<213> ORGANISM: Artificial Sequence
<220> FEATURE:
<223> OTHER INFORMATION: Description of Artificial Sequence: as in
      specification

<400> SEQUENCE: 26

```
gtcatttgga ggcacctctg ttttaagtta aagctatata tatatatata tatatatata     60
tatatatata tatatatata tatattcata ttttaatgat gtttaaaatc tatctaccct    120
ggggcttag                                                            129
```

<210> SEQ ID NO 27
<211> LENGTH: 169
<212> TYPE: DNA
<213> ORGANISM: Artificial Sequence
<220> FEATURE:
<223> OTHER INFORMATION: Description of Artificial Sequence: as in
      specification

<400> SEQUENCE: 27

```
tggtttgcag gaaaaattta gacagcacaa cagtggcgat tcatgatgaa gagatctact     60
gcaaatcctg ctacggaaag aagtatggac caaaaggcta tggttatggc cagggcgctg    120
gcacgctcaa catggaccgc ggtgagagac tgggcatcaa gccagagag                169
```

<210> SEQ ID NO 28
<211> LENGTH: 56
<212> TYPE: PRT
<213> ORGANISM: Artificial Sequence
<220> FEATURE:
<223> OTHER INFORMATION: Description of Artificial Sequence: as in
      specification

<400> SEQUENCE: 28

Val Cys Arg Lys Asn Leu Asp Ser Thr Thr Val Ala Ile His Asp Glu
 1               5                  10                  15

Glu Ile Tyr Cys Lys Ser Cys Tyr Gly Lys Lys Tyr Gly Pro Lys Gly
            20                  25                  30

Tyr Gly Tyr Gly Gln Gly Ala Gly Thr Leu Asn Met Asp Arg Gly Glu
        35                  40                  45

Arg Leu Gly Ile Lys Pro Glu Ser
    50                  55
```

<210> SEQ ID NO 29
<211> LENGTH: 448
<212> TYPE: DNA
<213> ORGANISM: Artificial Sequence
<220> FEATURE:
<223> OTHER INFORMATION: Description of Artificial Sequence: as in
      specification

<400> SEQUENCE: 29

```
gtgagagaat gttaccctct taaaagcggg tagaacagct cctgtcgctc aggcaccagg     60
agcctgcata tttagtttaa actaagcaag caaaataaaa tgtgacctct actaaatact    120
catatgatta ctacgacgtt ctgtaacgtc ataatattga cagttttgta tctaaaaatc    180
ttagtaatga atgcagggac ttctagcccc ggttatatag cattttaact gatatcagga    240
```

```
aaacataaat ctcaaggaac tgacttactt aatatcccat acgcactgga gatcaaatat      300
cttgaaatga gtgtctgaat tctgagatcg ttctcatatg attaactgtc cacggaaagt      360
ccttagtcac tctttcctca ggaaattaca tccttcaact tagaaattaa aaccatttcc      420
tcgttctgat gatttgaggg acaaatcg                                         448
```

<210> SEQ ID NO 30
<211> LENGTH: 306
<212> TYPE: DNA
<213> ORGANISM: Artificial Sequence
<220> FEATURE:
<223> OTHER INFORMATION: Description of Artificial Sequence: as in
      specification

<400> SEQUENCE: 30

```
aaatgtttca caatatacat tacctctaaa tcttcccatc aatgaaaact aaattcacaa       60 gaccccccaag gctgtgtttg tagccagaac tgggaaatca cggatgctct ttctgccctg     120
tccccacctt tcccagcaat aagcaagctc tgtgtgcacg ccctatgtgc agtggtaacc     180
ctgtctgtcc cttccagccg ggccctggtc tggtcttcct ctgcgatcag gtctaaggaa     240
ttcctcctcc cagaggtctt ctttaggact caaaaccatg gcctgccttt taacacacag     300
attaaa                                                                 306
```

<210> SEQ ID NO 31
<211> LENGTH: 69
<212> TYPE: DNA
<213> ORGANISM: Artificial Sequence
<220> FEATURE:
<223> OTHER INFORMATION: Description of Artificial Sequence: as in
      specification

<400> SEQUENCE: 31

```
cgaagctcct gttagctcag gaggaacatt tggagaaaca ctgcctcatt tttttctccg      60
ttcctccag                                                              69
```

<210> SEQ ID NO 32
<211> LENGTH: 130
<212> TYPE: DNA
<213> ORGANISM: Artificial Sequence
<220> FEATURE:
<223> OTHER INFORMATION: Description of Artificial Sequence: as in
      specification

<400> SEQUENCE: 32

```
tgctcaacct cacaggccta cgacaaatcc aaacacttct aaatttgccc agaaatatgg      60
aggagctgag aagtgttcca ggtgtgggga ttccgtgtat gctgcggaga agatcattgg     120
agctgggaag                                                             130
```

<210> SEQ ID NO 33
<211> LENGTH: 43
<212> TYPE: PRT
<213> ORGANISM: Artificial Sequence
<220> FEATURE:
<223> OTHER INFORMATION: Description of Artificial Sequence: as in
      specification

<400> SEQUENCE: 33

Ala Gln Pro His Arg Pro Thr Thr Asn Pro Asn Thr Ser Lys Phe Ala
 1               5                  10                  15

Gln Lys Tyr Gly Gly Ala Glu Lys Cys Ser Arg Cys Gly Asp Ser Val

Tyr Ala Ala Glu Lys Ile Ile Gly Ala Gly Lys
            35                  40

<210> SEQ ID NO 34
<211> LENGTH: 142
<212> TYPE: DNA
<213> ORGANISM: Artificial Sequence
<220> FEATURE:
<223> OTHER INFORMATION: Description of Artificial Sequence: as in
      specification

<400> SEQUENCE: 34
gtagggcgct gtctctaagt ggtaactgca gcacacactc acacacacac agggtgctgt    60
ctgtctctaa ctggtaactg taataaacac acacatacat acacaagcat acatagacac   120
acacacacac acacacacat ac                                            142

<210> SEQ ID NO 35
<211> LENGTH: 188
<212> TYPE: DNA
<213> ORGANISM: Murinae gen. sp.

<400> SEQUENCE: 35
ctgctcccag caaacagccc tttactggtg gctagaagat atgacagcaa agaggccagc    60
tttctagctg agccaaaccg tagcctgagg aggctgcttg tgcgctggtt ttcccagcca   120
cttgctgcat ctagatcgag ccaaaggaaa caagcctctc aatgtcctaa ctcagctgtc   180
tcttccag                                                            188

<210> SEQ ID NO 36
<211> LENGTH: 94
<212> TYPE: DNA
<213> ORGANISM: Murinae gen. sp.

<400> SEQUENCE: 36
ccctggcaca aaaactgttt ccggtgtgcc aagtgtggga agagtctgga gtctacaact    60
ctgactgaga agaaggcga aatctactgt aaag                                 94

<210> SEQ ID NO 37
<211> LENGTH: 32
<212> TYPE: PRT
<213> ORGANISM: Murinae gen. sp.

<400> SEQUENCE: 37

Pro Trp His Lys Asn Cys Phe Arg Cys Ala Lys Cys Gly Lys Ser Leu
 1               5                  10                  15

Glu Ser Thr Thr Leu Thr Glu Lys Glu Gly Glu Ile Tyr Cys Lys Gly
                20                  25                  30

<210> SEQ ID NO 38
<211> LENGTH: 471
<212> TYPE: DNA
<213> ORGANISM: Murinae gen. sp.

<400> SEQUENCE: 38
gtaaaaactc ggttctgctg tctgttagtg tcaccagaaa gggagacatc gtgcactgtt    60 acctttttgaa aatgagaccg acatcttagg acagtgatta cttcttccat tcctactgtg   120
tgtgttaagt ccacacggct ggggatctgg ccgaatggta aaagcttgcc tatgtagcac   180
attcacaagg aggccacgct cagcacggcc tccccaacct ctgacttcct gctttaagcc   240

```
aagcatatga ctacgtgagg gtgacacaca gaaggcagct ggatttcagc ctgcagctca    300
tcacaatcct aacttggatg ccgtgggaat tcctggactc gcttcaaaca aggatgctca    360
tagcagagcc cattttatat cttaaactga cctctgcaga gcctccagtt ggcttttaaa    420
ttaatggcca tttgttagtg acctctgatt aactctccct ttcctttgta g             471

<210> SEQ ID NO 39
<211> LENGTH: 283
<212> TYPE: DNA
<213> ORGANISM: Murinae gen. sp.

<400> SEQUENCE: 39
ggtgctacgc aaagaacttt gggcccaagg gatttggcta tggtcaaggg gcaggggccc     60
ttgttcatgc tcagtaatgg tgtgaaccag taagcacgac agagaatctc cattaccaaa    120
ctgcagatgc cgtttatggc gctcactact gtgaaacagc cagcacttgg cactgggcat    180
caccgagctg cctgtggggg ctggaccgac agcgctgcac tctcccgccc actcactagc    240
gtctaagagc attcttttac atttgaaata aatttttggc ttg                      283

<210> SEQ ID NO 40
<211> LENGTH: 24
<212> TYPE: PRT
<213> ORGANISM: Artificial Sequence
<220> FEATURE:
<223> OTHER INFORMATION: murinae gen. sp.

<400> SEQUENCE: 40

Cys Tyr Ala Lys Asn Phe Gly Pro Lys Gly Phe Gly Tyr Gly Gln Gly
 1               5                  10                  15

Ala Gly Ala Leu Val His Ala Gln
            20

<210> SEQ ID NO 41
<211> LENGTH: 8
<212> TYPE: DNA
<213> ORGANISM: Artificial Sequence
<220> FEATURE:
<223> OTHER INFORMATION: consensus
<220> FEATURE:
<223> OTHER INFORMATION: Description of Artificial Sequence:consensus

<400> SEQUENCE: 41 yaytcyyy                                                               8

<210> SEQ ID NO 42
<211> LENGTH: 6
<212> TYPE: DNA
<213> ORGANISM: Artificial Sequence
<220> FEATURE:
<223> OTHER INFORMATION: Description of Artificial Sequence: yaytcyyy
      consensus

<400> SEQUENCE: 42 tttaaa                                                                 6

<210> SEQ ID NO 43
<211> LENGTH: 5
<212> TYPE: DNA
<213> ORGANISM: Artificial Sequence
<220> FEATURE:
<223> OTHER INFORMATION: Description of Artificial Sequence: ccatt box
```

```
<400> SEQUENCE: 43 ccaat                                                              5

<210> SEQ ID NO 44
<211> LENGTH: 6
<212> TYPE: DNA
<213> ORGANISM: Artificial Sequence
<220> FEATURE:
<223> OTHER INFORMATION: Description of Artificial Sequence: e box
<220> FEATURE:
<221> NAME/KEY: variation
<222> LOCATION: (1)..(6)
<223> OTHER INFORMATION: where n can be any nucleotide

<400> SEQUENCE: 44 canntg                                                             6

<210> SEQ ID NO 45
<211> LENGTH: 9
<212> TYPE: DNA
<213> ORGANISM: Artificial Sequence
<220> FEATURE:
<223> OTHER INFORMATION: Description of Artificial Sequence: gggrntyyc
<220> FEATURE:
<221> NAME/KEY: variation
<222> LOCATION: (1)..(9)
<223> OTHER INFORMATION: where n can be any nucleotide

<400> SEQUENCE: 45 gggrntyyc                                                          9

<210> SEQ ID NO 46
<211> LENGTH: 5
<212> TYPE: DNA
<213> ORGANISM: Artificial Sequence
<220> FEATURE:
<223> OTHER INFORMATION: Description of Artificial Sequence: artif:
      peptide

<400> SEQUENCE: 46 caccc                                                              5
```